United States Patent [19]
Okorocha et al.

[11] Patent Number: 5,634,584
[45] Date of Patent: Jun. 3, 1997

[54] SURGICAL INSTRUMENT

[75] Inventors: Livyn O. Okorocha; Sean P. Conlon, both of Cincinnati, Ohio

[73] Assignee: Ethicon Endo-Surgery, Inc., Cincinnati, Ohio

[21] Appl. No.: 652,149

[22] Filed: May 23, 1996

Related U.S. Application Data

[60] Division of Ser. No. 259,322, Jun. 10, 1994, Pat. No. 5,601,224, which is a continuation-in-part of Ser. No. 959,184, Oct. 9, 1992, Pat. No. 5,381,943.

[51] Int. Cl.$^6$ .............................................. A61B 17/068
[52] U.S. Cl. .................... 227/176.1; 227/19; 227/179.1
[58] Field of Search ............................. 227/175.1, 176.1, 227/178.1, 19

[56] References Cited

U.S. PATENT DOCUMENTS

| | | |
|---|---|---|
| Re. 28,932 | 8/1976 | Noiles et al. . |
| Re. 33,362 | 10/1990 | Mongeon et al. . |
| 389,660 | 9/1888 | Mandel et al. . |

(List continued on next page.)

FOREIGN PATENT DOCUMENTS

| | | | |
|---|---|---|---|
| 39560 | 11/1981 | European Pat. Off. . | |
| 40157 | 11/1981 | European Pat. Off. . | |
| 0116220A1 | 8/1984 | European Pat. Off. | A61B 17/12 |
| 324166 | 9/1989 | European Pat. Off. . | |
| 549187 | 8/1991 | European Pat. Off. . | |
| 0484677A1 | 5/1992 | European Pat. Off. | A61B 17/072 |
| 557806 | 1/1993 | European Pat. Off. . | |
| 567146 | 10/1993 | European Pat. Off. . | |
| 582295 | 2/1994 | European Pat. Off. . | |
| 2681775 | 4/1993 | France . | |
| 2330182 | 1/1975 | Germany . | |
| 2703529 | 8/1978 | Germany . | |
| 3301713A1 | 7/1984 | Germany | A61B 17/11 |
| 4215449 | 2/1993 | Germany . | |
| 9366161 | 4/1993 | Germany . | |
| 4325462 | 2/1994 | Germany . | |
| 2151142 | 11/1994 | United Kingdom . | |
| WO88/01486 | 3/1988 | WIPO . | |
| WO89/04144 | 5/1989 | WIPO . | |
| WO92/14412 | 9/1992 | WIPO . | |

OTHER PUBLICATIONS

Article, Swain, C.P., Mills, T.N. "An Endoscopic Sewing Machine", *Gastro-intestinal Endoscopy*, 1986, vol. 32, No. 1, pp. 36–38.

Article, Swain, C.P., Brown, G.J., and Mills, T.N., "an Encoscopic Stapling Device: The Development of a New Flexible Endoscopically Controlled Device for Placing Multiple Transmural Staples in Gastrointestinal Tissue", *Gastrointestinal Endoscopy*, 1989, vol. 35, No. 4, pp. 338–339.

(List continued on next page.)

*Primary Examiner*—Scott A. Smith
*Attorney, Agent, or Firm*—Dressler, Goldsmith, Shore & Milnamow, Ltd.

[57] ABSTRACT

Various mechanisms are provided for use in a surgical instrument. A shaft and an engaged lost motion operating knob are provided for rotation relative to a handle portion. A latch system prevents rotation of the shaft unless the shaft is rotated by the knob. A cartridge is provided for rotation at the distal end of the shaft. Engaging structures are provided for preventing rotation of the cartridge relative to the shaft when axial forces are applied to the cartridge. A loading tool is provided for engaging the cartridge to install the cartridge on the instrument. The cartridge includes a washer for engaging a carrier on which the cartridge is mounted so as to prevent rotation of the washer. The washer is adapted to engage a fastener advancing member in a first angular orientation and is disengaged when the cartridge is rotated to establish a second relative angular orientation. In the first angular orientation, the fastener advancing member is restrained against longitudinal movement to assist in installation of the cartridge onto the instrument. The distal end of the instrument can be articulated, and a helical gear operator is provided for effecting the articulation.

2 Claims, 18 Drawing Sheets

U.S. PATENT DOCUMENTS

| | | |
|---|---|---|
| 2,028,635 | 1/1936 | Wappler . |
| 2,427,873 | 9/1947 | Peterson . |
| 2,507,710 | 5/1950 | Grosso . |
| 2,707,783 | 5/1955 | Sullivan . |
| 3,054,406 | 9/1962 | Usher . |
| 3,124,136 | 3/1964 | Usher . |
| 3,256,875 | 6/1966 | Tsepelev . |
| 3,314,431 | 4/1967 | Smith, Jr. . |
| 3,494,533 | 2/1970 | Green et al. . |
| 3,593,903 | 7/1971 | Astafiev et al. ............................ 227/76 |
| 3,643,851 | 2/1972 | Green et al. . |
| 3,763,860 | 10/1973 | Clarke . |
| 3,777,538 | 12/1973 | Weatherly et al. . |
| 3,837,555 | 9/1974 | Green . |
| 3,871,379 | 3/1975 | Clarke . |
| 3,955,581 | 5/1976 | Spasiano et al. . |
| 4,014,492 | 3/1977 | Rothfuss . |
| 4,043,504 | 8/1977 | Hueil et al. . |
| 4,127,227 | 11/1978 | Green . |
| 4,196,836 | 4/1980 | Becht . |
| 4,204,233 | 5/1980 | Kruy . |
| 4,204,623 | 5/1980 | Green . |
| 4,207,510 | 6/1980 | Hiltebrandt . |
| 4,256,251 | 3/1981 | Moshofsky . |
| 4,261,244 | 4/1981 | Becht et al. . |
| 4,316,468 | 2/1982 | Klieman et al. . |
| 4,317,535 | 3/1982 | Huftel et al. . |
| 4,321,002 | 3/1982 | Froehlich . |
| 4,347,847 | 9/1982 | Usher . |
| 4,349,828 | 9/1982 | Green . |
| 4,375,866 | 3/1983 | Giersch et al. . |
| 4,399,810 | 8/1983 | Samuels et al. . |
| 4,403,693 | 9/1983 | Froehlich . |
| 4,406,392 | 9/1983 | Campbell et la. . |
| 4,407,286 | 10/1983 | Noiles et al. . |
| 4,427,008 | 1/1984 | Tronsue . |
| 4,452,245 | 6/1984 | Usher . |
| 4,470,532 | 9/1984 | Froehlich . |
| 4,485,816 | 12/1984 | Kurmme . |
| 4,485,953 | 12/1984 | Rothfuss . |
| 4,489,875 | 12/1984 | Crawford et al. . |
| 4,496,090 | 1/1985 | Crevier et al. . |
| 4,505,273 | 3/1985 | Braun et al. . |
| 4,506,819 | 3/1985 | Rand ........................ 227/120 |
| 4,509,518 | 4/1985 | McGarry et al. . |
| 4,520,817 | 6/1985 | Green . |
| 4,523,695 | 6/1985 | Braun et al. . |
| 4,523,707 | 6/1985 | Blake, III et al. . |
| 4,526,174 | 7/1985 | Froehlich . |
| 4,527,724 | 7/1985 | Chow et al. . |
| 4,532,927 | 8/1985 | Miksza, Jr. . |
| 4,550,715 | 11/1985 | Santagelo et al. . |
| 4,562,839 | 1/1986 | Blake, III et al. . |
| 4,566,620 | 1/1986 | Green . |
| 4,573,622 | 3/1986 | Green et al. ............................... 227/19 |
| 4,583,670 | 4/1986 | Alvarado . |
| 4,591,086 | 5/1986 | Campbell et al. . |
| 4,592,498 | 6/1986 | Braun et al. . |
| 4,596,350 | 6/1986 | Smith et al. . |
| 4,607,638 | 8/1986 | Crainich . |
| 4,610,251 | 9/1986 | Kumar . |
| 4,610,383 | 9/1986 | Rothfuss et al. . |
| 4,616,650 | 10/1986 | Green et al. . |
| 4,618,086 | 10/1986 | Li et al. . |
| 4,619,391 | 10/1986 | Sharkany et al. . |
| 4,624,254 | 11/1986 | McGarry et al. . |
| 4,634,035 | 1/1987 | Li et al. . |
| 4,646,751 | 3/1987 | Maslanka . |
| 4,655,221 | 4/1987 | Devereux . |
| 4,662,373 | 5/1987 | Montgomery et al. . |
| 4,662,555 | 5/1987 | Thornton . |
| 4,664,305 | 5/1987 | Blake, III et al. . |
| 4,665,906 | 5/1987 | Jervis . |
| 4,671,279 | 6/1987 | Hill . |
| 4,688,555 | 8/1987 | Wardle . |
| 4,691,853 | 9/1987 | Storace . |
| 4,706,655 | 11/1987 | Krauter . |
| 4,706,668 | 11/1987 | Backer ..................................... 128/325 |
| 4,719,917 | 1/1988 | Barrows et al. . |
| 4,728,020 | 3/1988 | Green et al. . |
| 4,747,531 | 5/1988 | Brinkerhoff et al. . |
| 4,754,909 | 7/1988 | Barker et al. . |
| 4,763,669 | 8/1988 | Jaeger . |
| 4,784,137 | 11/1988 | Kulik et al. . |
| 4,787,387 | 11/1988 | Burbank, III et al. . |
| 4,789,090 | 12/1988 | Blake, III . |
| 4,796,793 | 1/1989 | Smith et al. . |
| 4,802,478 | 2/1989 | Powell . |
| 4,807,628 | 2/1989 | Peters et al. . |
| 4,821,939 | 4/1989 | Green . |
| 4,821,942 | 4/1989 | Richards et al. . |
| 4,838,884 | 6/1989 | Dumican et al. . |
| 4,841,888 | 6/1989 | Mills et al. . |
| 4,869,414 | 9/1989 | Green et al. . |
| 4,872,456 | 10/1989 | Hasson . |
| 4,874,122 | 10/1989 | Froelich et al. . |
| 4,880,015 | 11/1989 | Nierman . |
| 4,899,745 | 2/1990 | Laboureau et al. . |
| 4,919,112 | 4/1990 | Siegmund . |
| 4,919,152 | 4/1990 | Ger . |
| 4,919,320 | 4/1990 | Storace . |
| 4,934,364 | 6/1990 | Green . |
| 4,944,443 | 7/1990 | Oddsen et al. . |
| 4,951,860 | 8/1990 | Peters et al. . |
| 4,951,861 | 8/1990 | Schulze et al. . |
| 4,978,049 | 12/1990 | Green . |
| 4,991,763 | 2/1991 | Storace . |
| 4,997,463 | 3/1991 | Oberlander . |
| 5,002,551 | 3/1991 | Linsky et al. . |
| 5,015,249 | 5/1991 | Nakao et al. . |
| 5,018,657 | 5/1991 | Pedlick et al. . |
| 5,040,715 | 8/1991 | Green et al. . |
| 5,042,707 | 8/1991 | Taheri . |
| 5,047,038 | 9/1991 | Peters et al. . |
| 5,049,153 | 9/1991 | Nakao et al. . |
| 5,071,430 | 12/1991 | de Salis et al. . |
| 5,084,057 | 1/1992 | Green et al. . |
| 5,100,420 | 3/1992 | Green et al. . |
| 5,125,553 | 6/1992 | Oddsen et al. . |
| 5,147,373 | 9/1992 | Ferzli ...................................... 606/144 |
| 5,161,725 | 11/1992 | Murray . |
| 5,163,945 | 11/1992 | Ortiz et al. ............................... 606/142 |
| 5,170,926 | 12/1992 | Ruckdeschel et al. . |
| 5,174,276 | 12/1992 | Cockard . |
| 5,174,487 | 12/1992 | Rothfuss et al. . |
| 5,176,702 | 1/1993 | Bales et al. .............................. 606/208 |
| 5,190,203 | 3/1993 | Rodak . |
| 5,209,747 | 5/1993 | Knaepfler . |
| 5,217,472 | 6/1993 | Green et al. . |
| 5,222,975 | 6/1993 | Crainich . |
| 5,254,130 | 10/1993 | Poncet et al. . |
| 5,257,713 | 11/1993 | Green et al. . |
| 5,258,008 | 11/1993 | Wilk . |
| 5,271,385 | 12/1993 | Bailey . |
| 5,275,608 | 1/1994 | Forman . |
| 5,289,963 | 3/1994 | McGarry et al. . |
| 5,307,976 | 5/1994 | Olson et al. . |
| 5,312,023 | 5/1994 | Green et al. . |
| 5,337,937 | 8/1994 | Remiszewski et al. . |
| 5,356,064 | 10/1994 | Green et al. ............................ 227/177 |
| 5,452,836 | 9/1995 | Huitema et al. . |
| 5,465,894 | 11/1995 | Clark et al. . |

OTHER PUBLICATIONS

Publication Entitled "A Quick Stapler Tie–Over Fixation For Skin Grafts", by Haim Y. Kaplan, M.D., Ann. Plast. Surg. 22:173, 1989, pp. 173–174.

Publication Entitled "A Rapid and Effective Method of Skin Graft Stabilization in Burned Children", by J. B. Boyd et al., The Hospital For Sick Children, Toronto, Canada, 1982, pp. 400–401.

Publication Entitled "A Simple Bolster Technique For Skin Grafting", by Henry T. Hoffman, M.D. and Michael LaRouer, M.D., Department of Otolaryngology, University of Michigan, Laryngoscope 99, May, 1989, p, 558.

M–D–D–I Report, Sep. 1991 Ethicon Endoscopic Staple for Hernia Repair.

Publication Entitled Shape Memory Alloys From Scientific American, Nov. 1979.

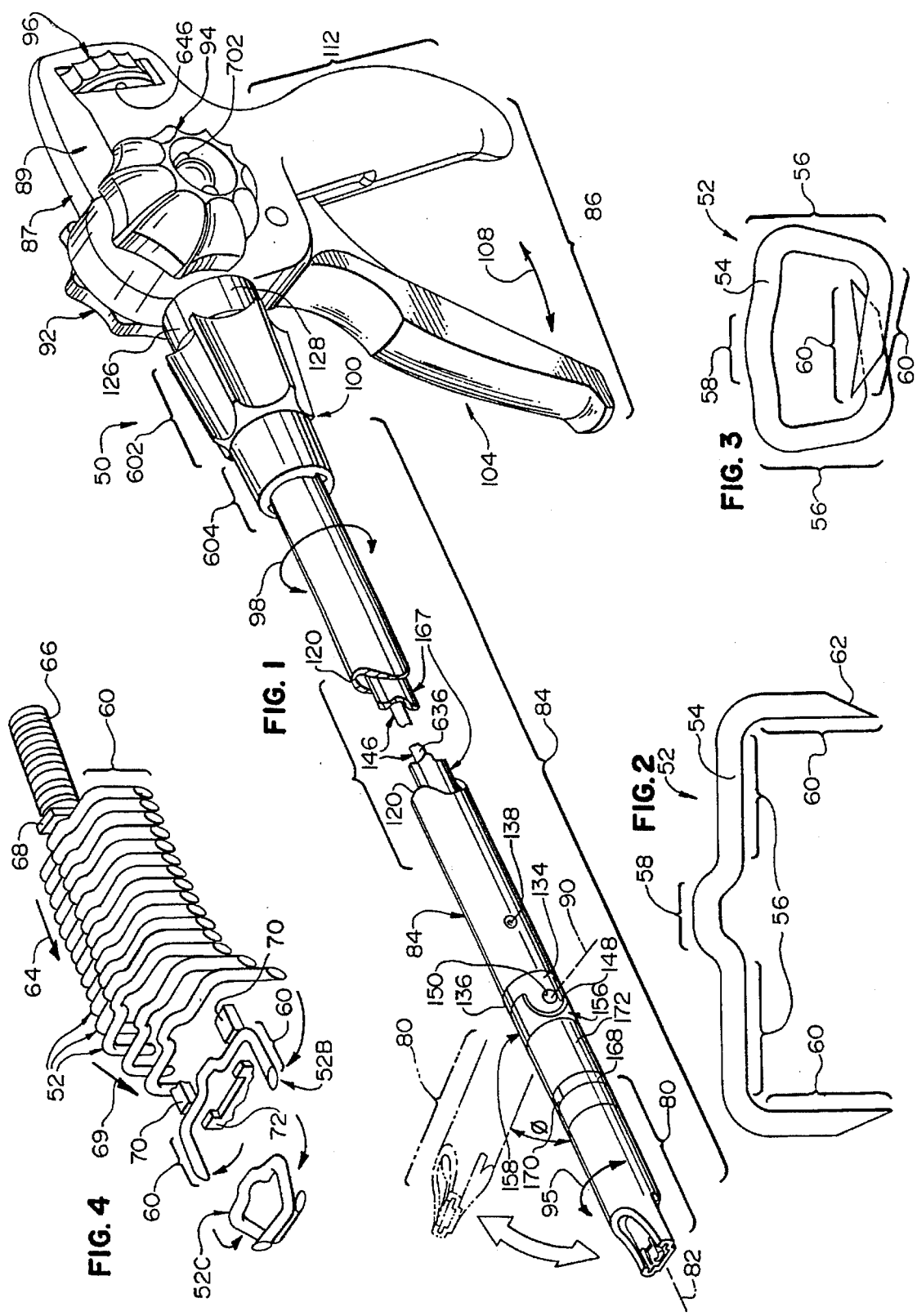

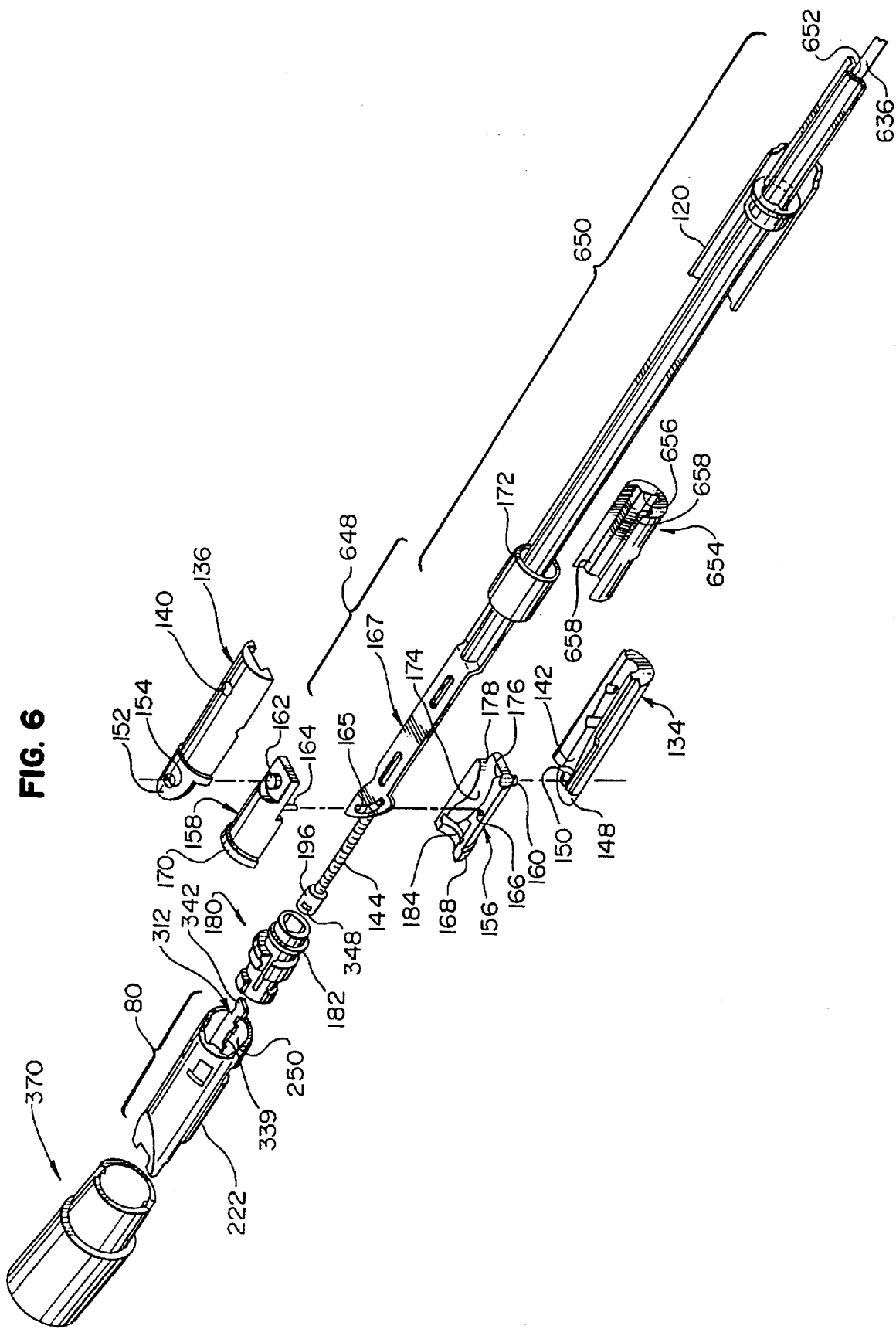

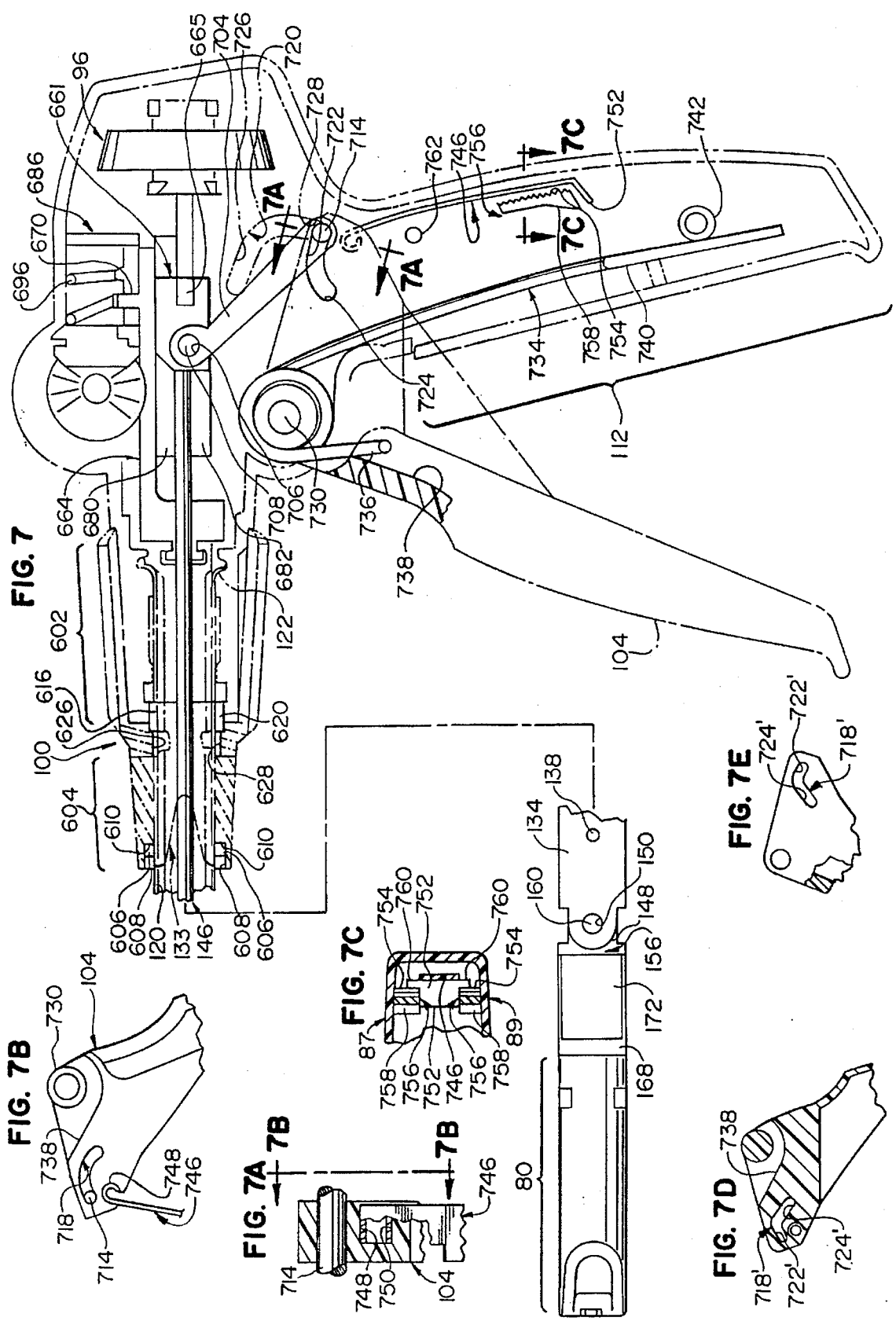

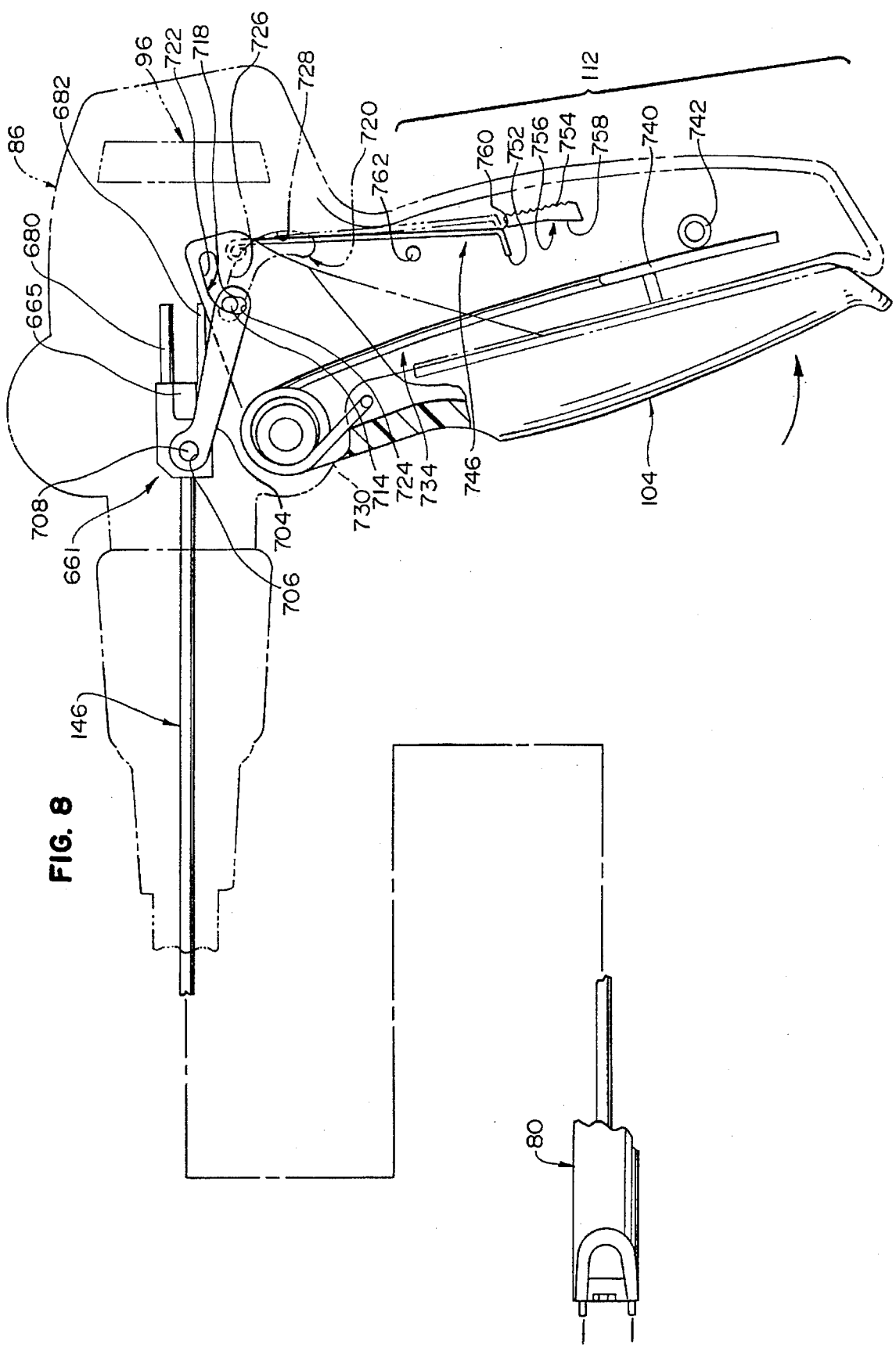

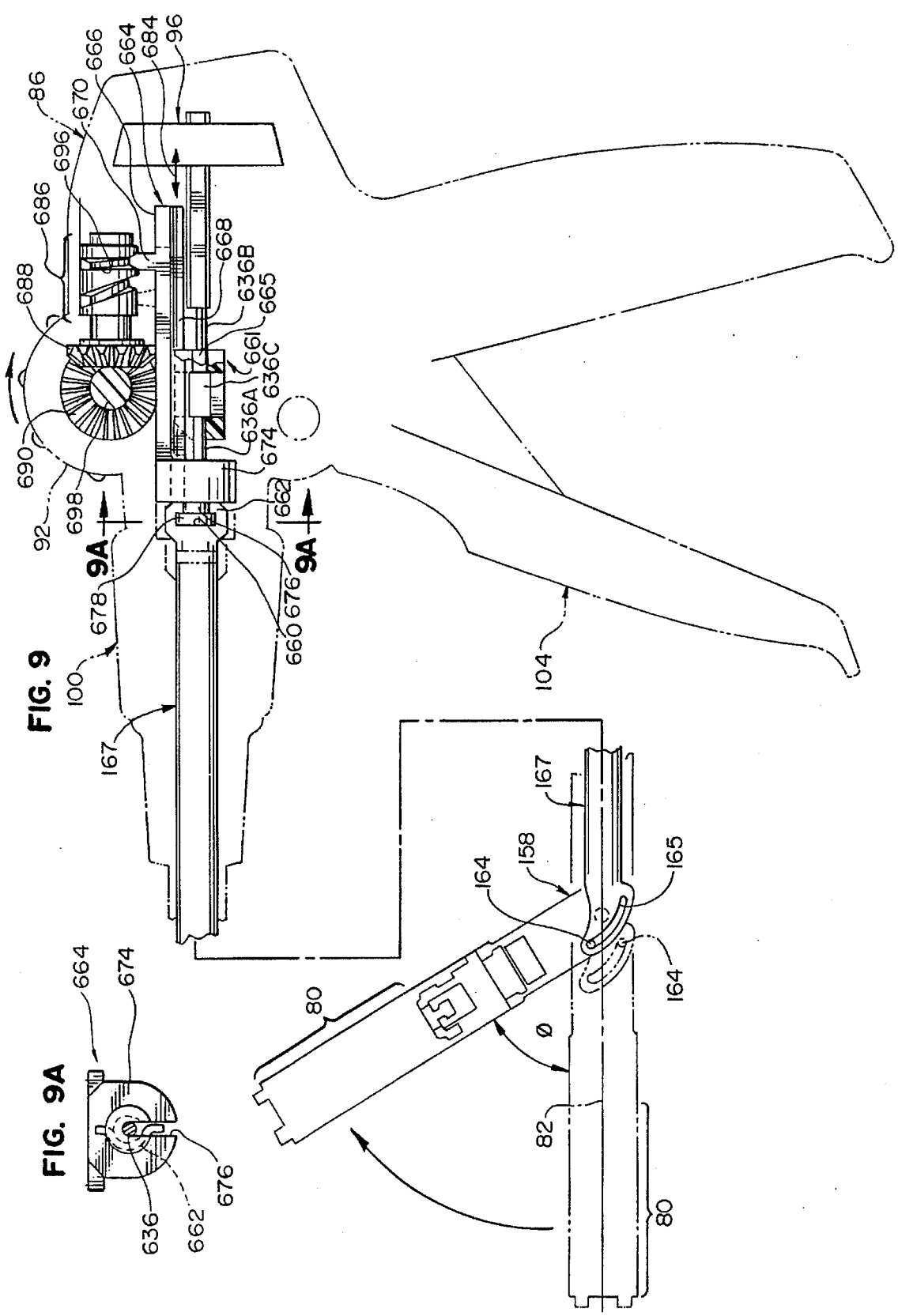

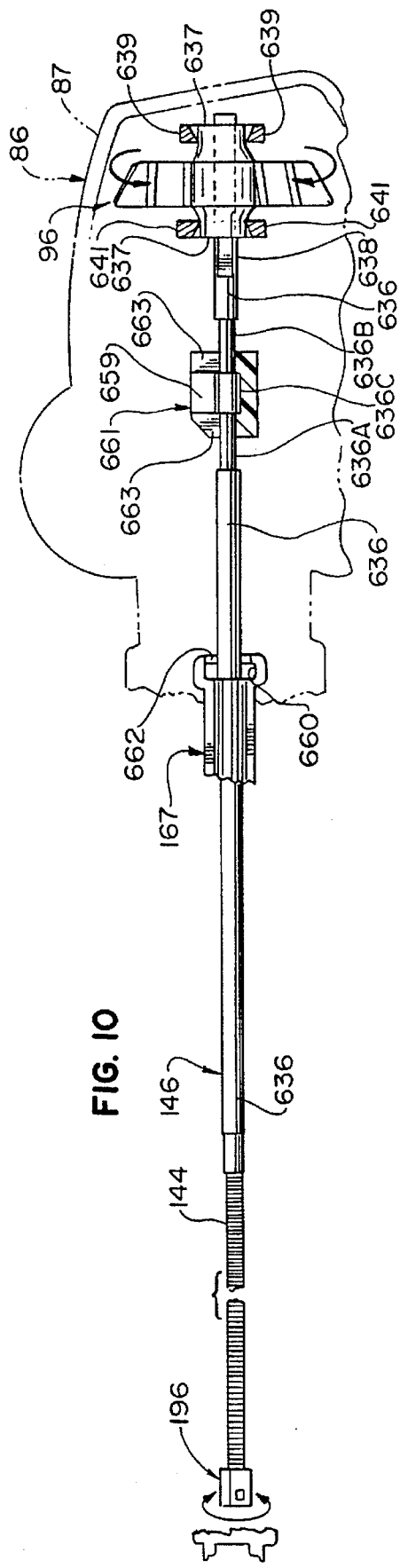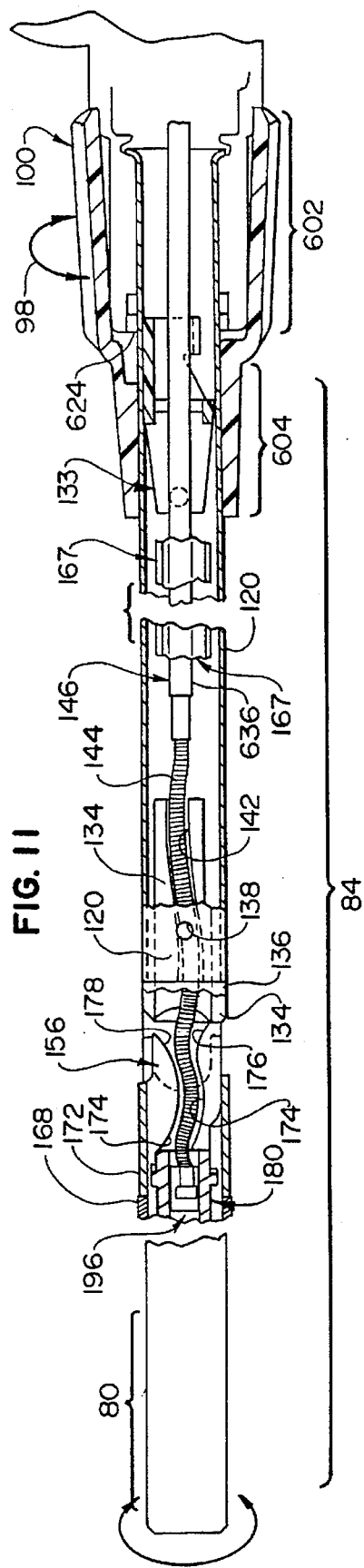

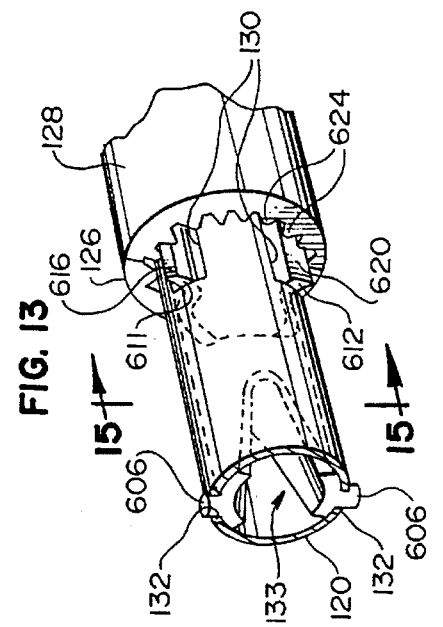
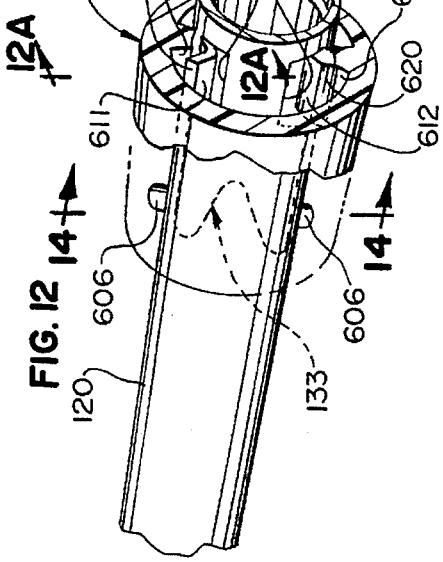
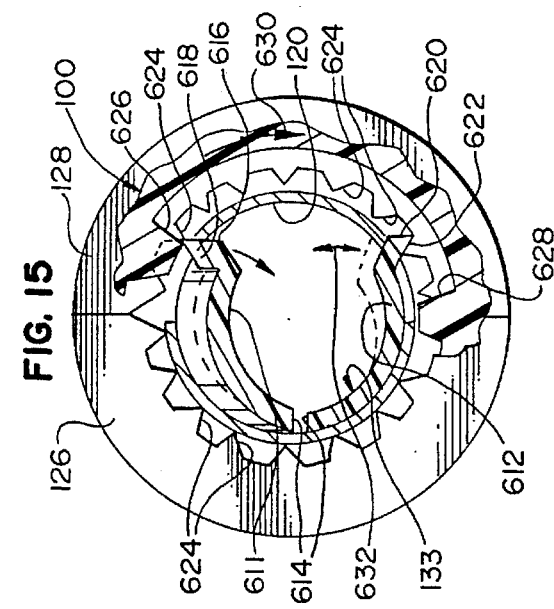
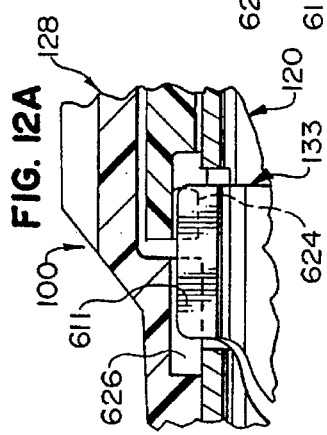
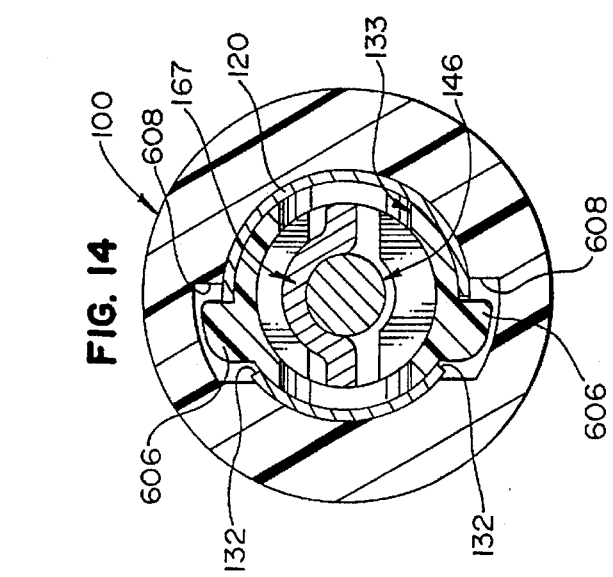

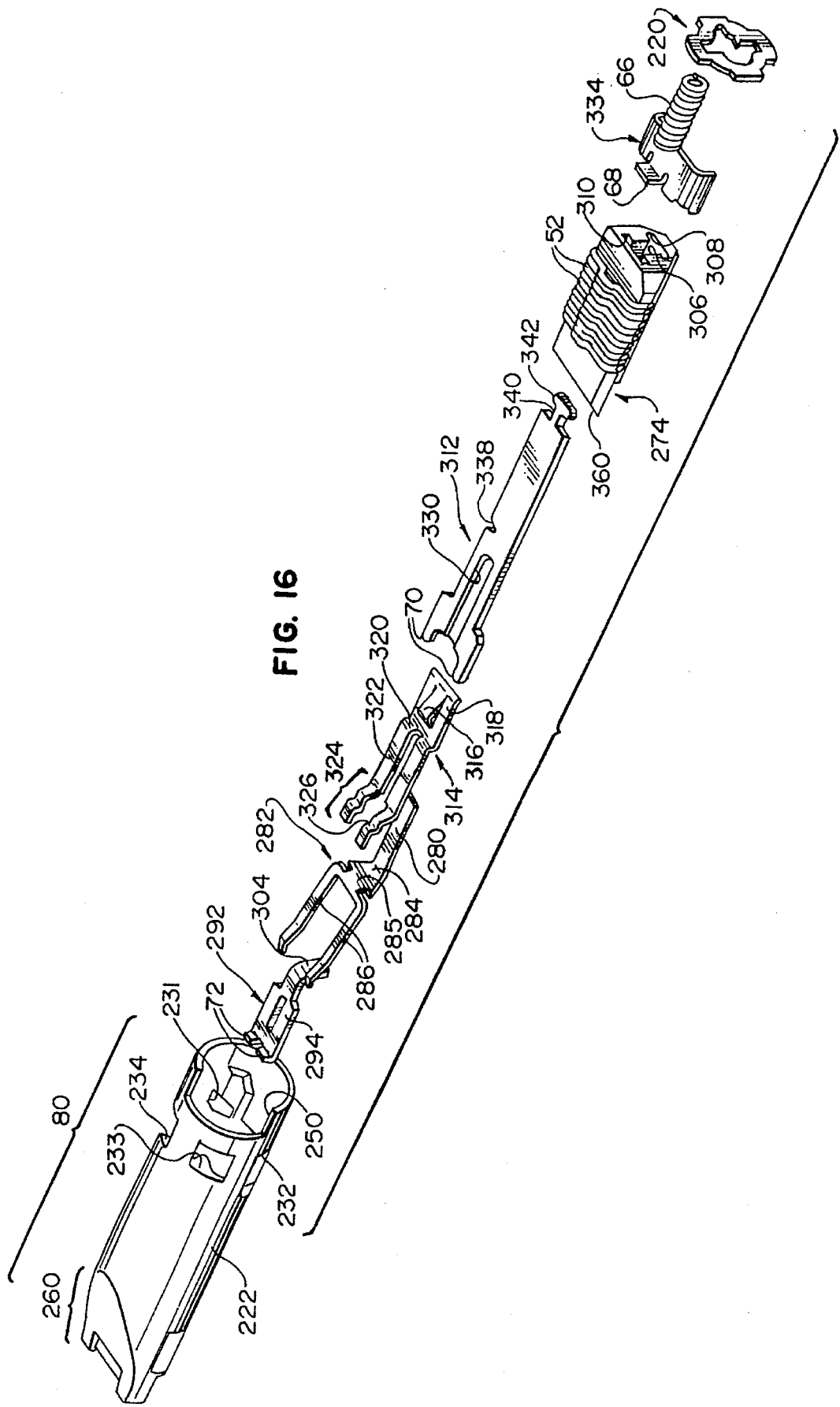

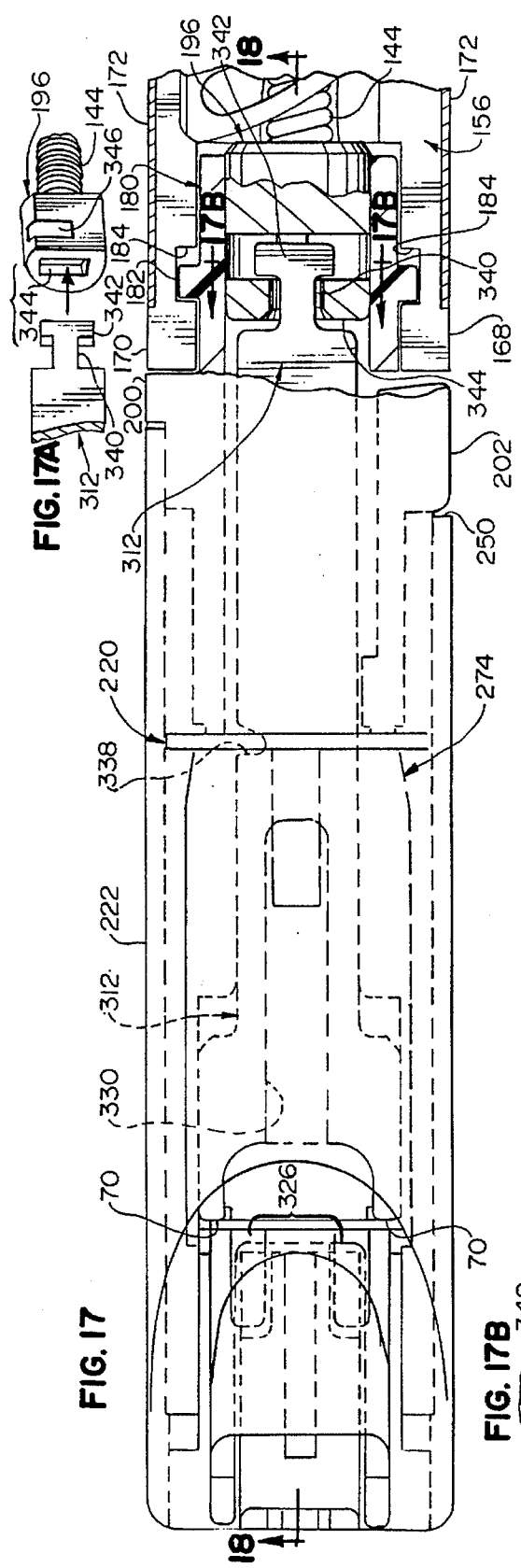
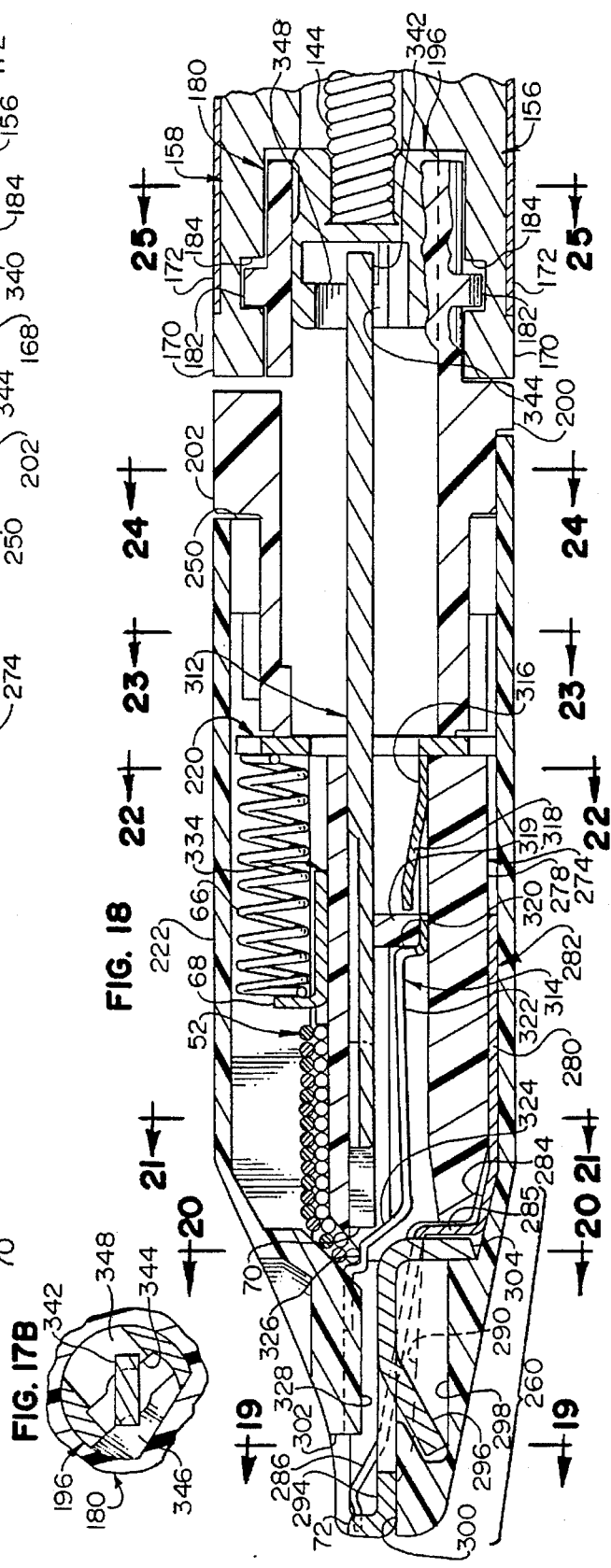

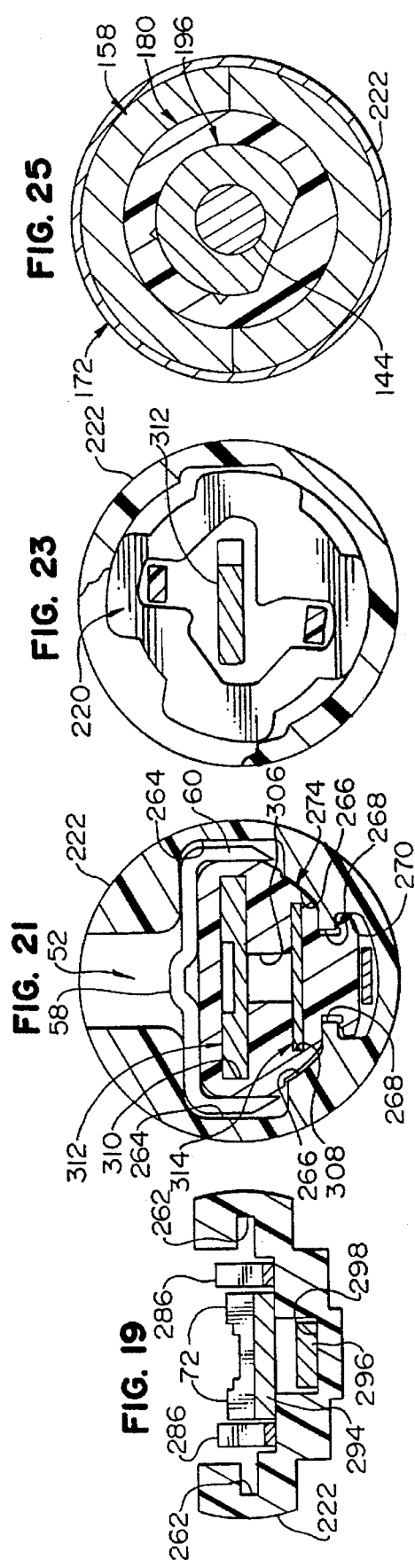

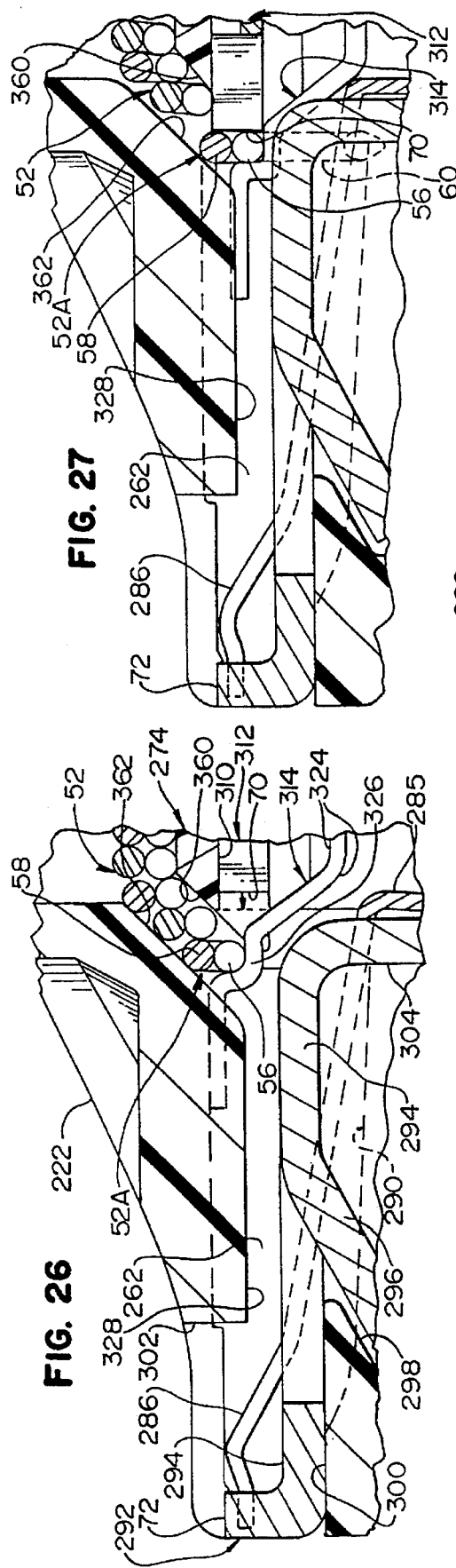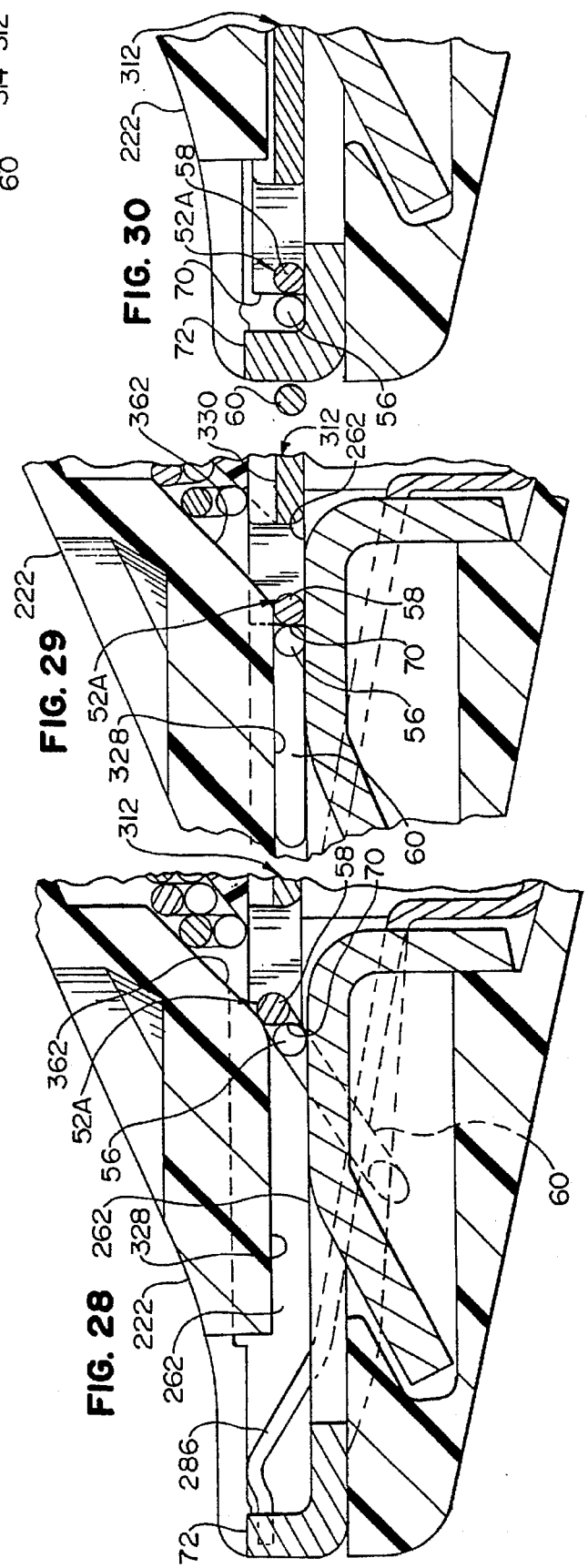

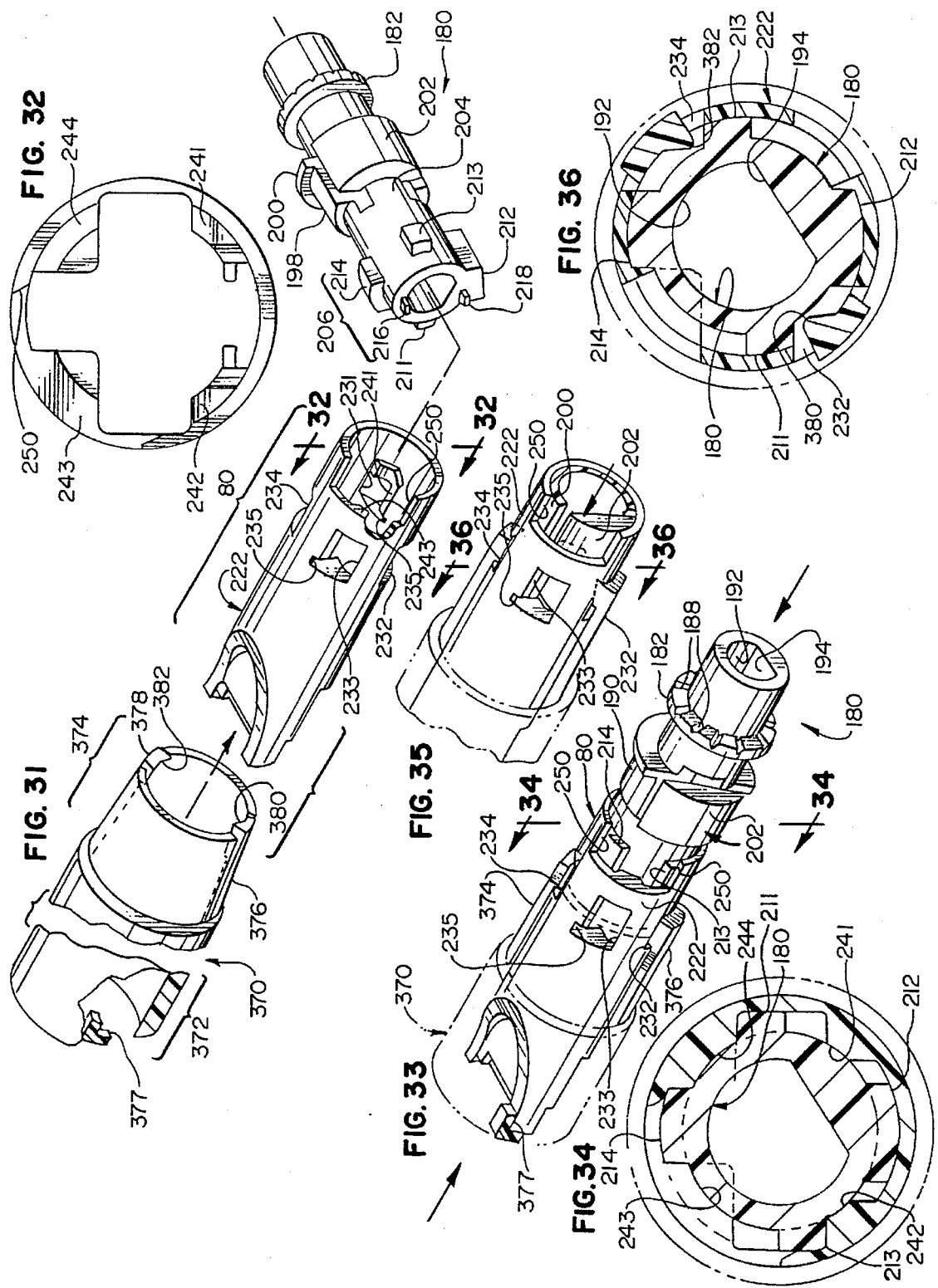

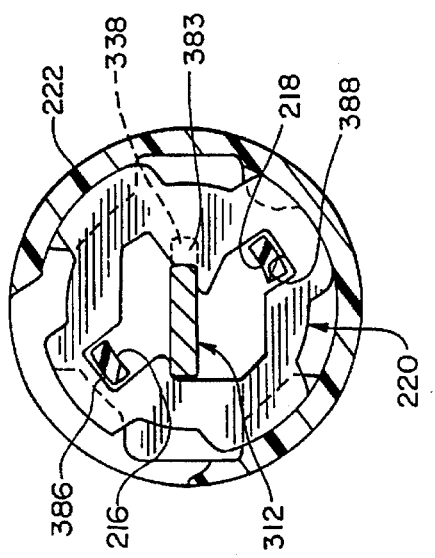
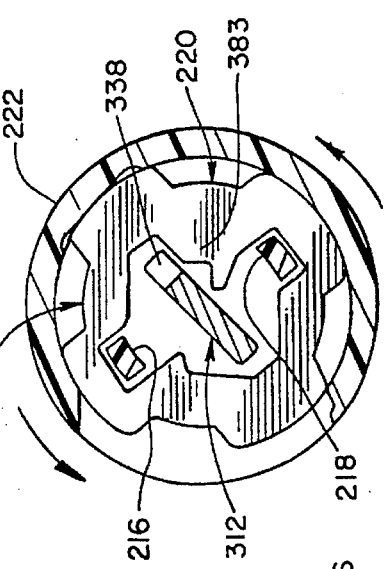
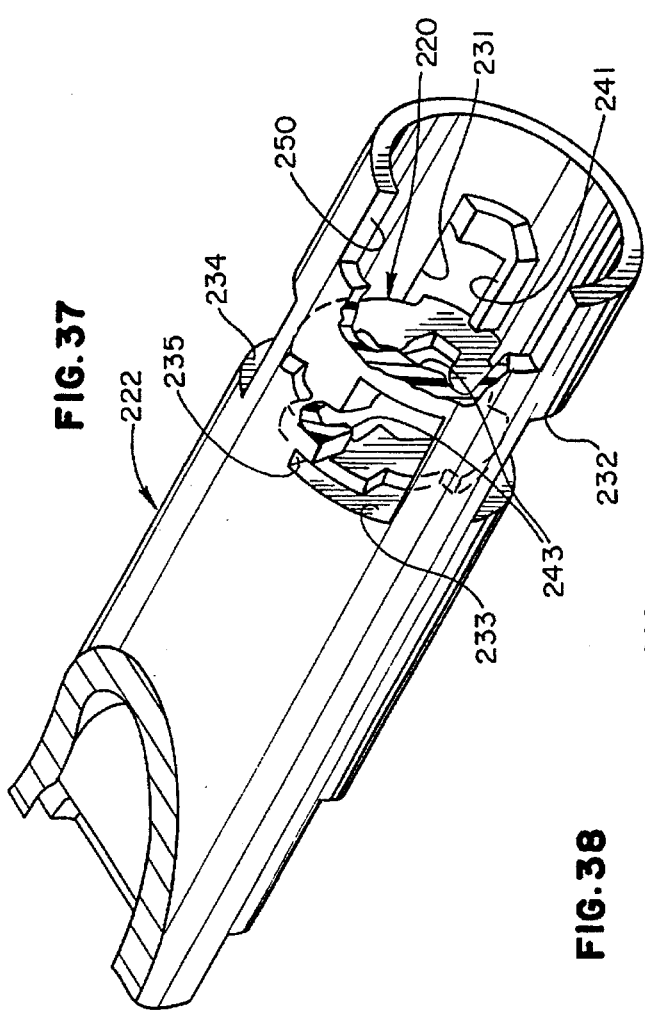
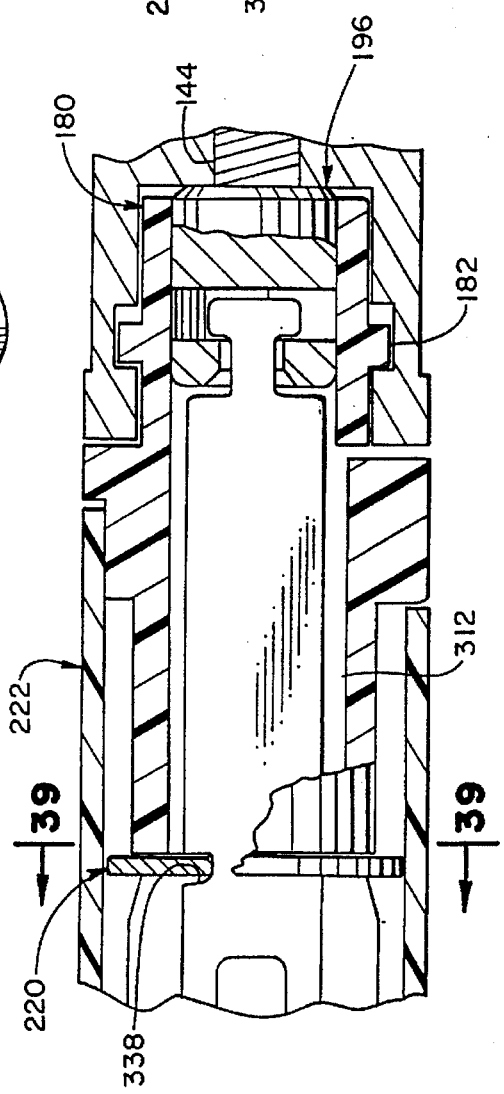

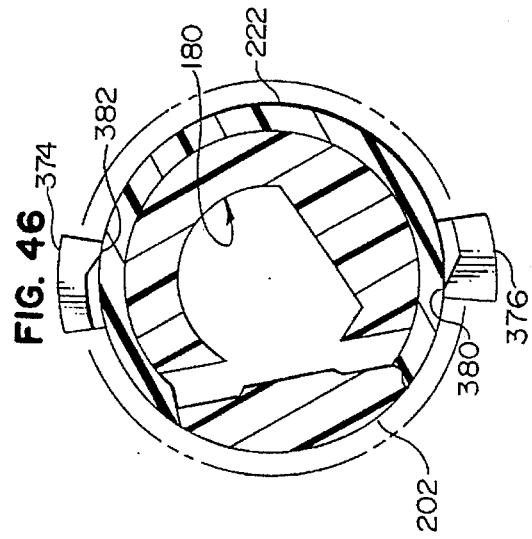
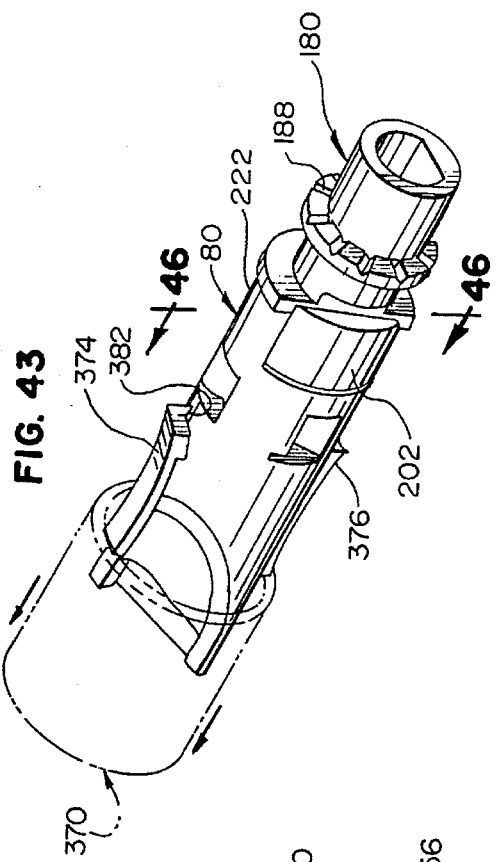
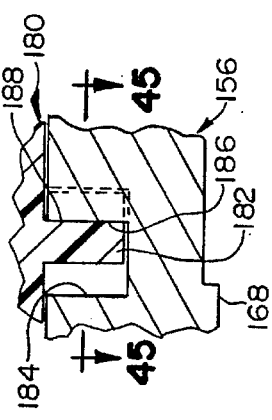
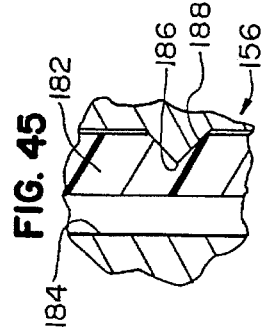
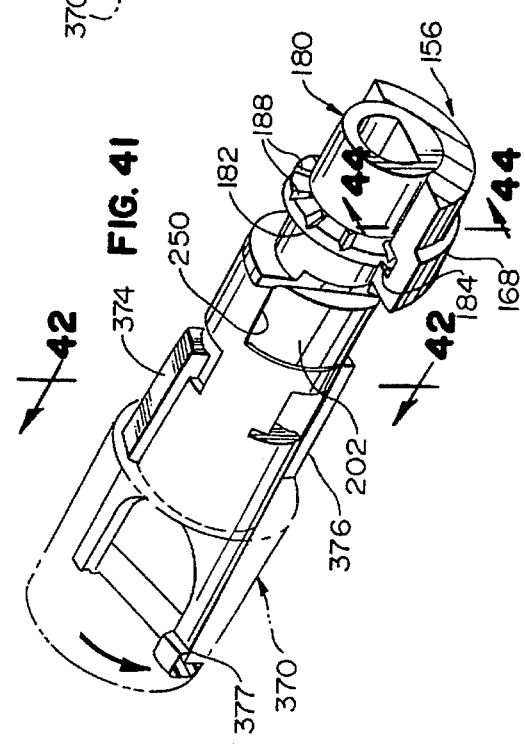
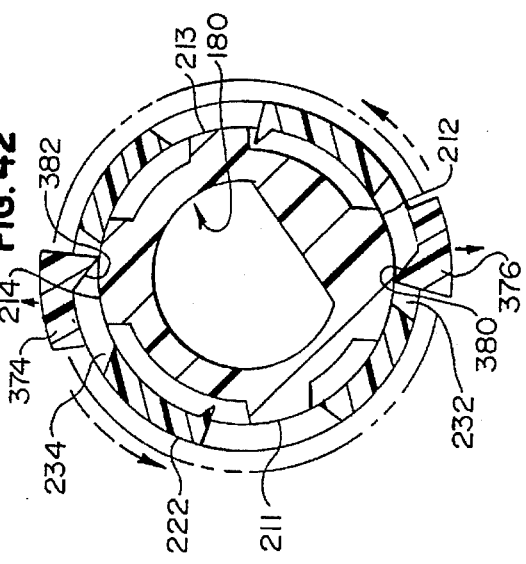

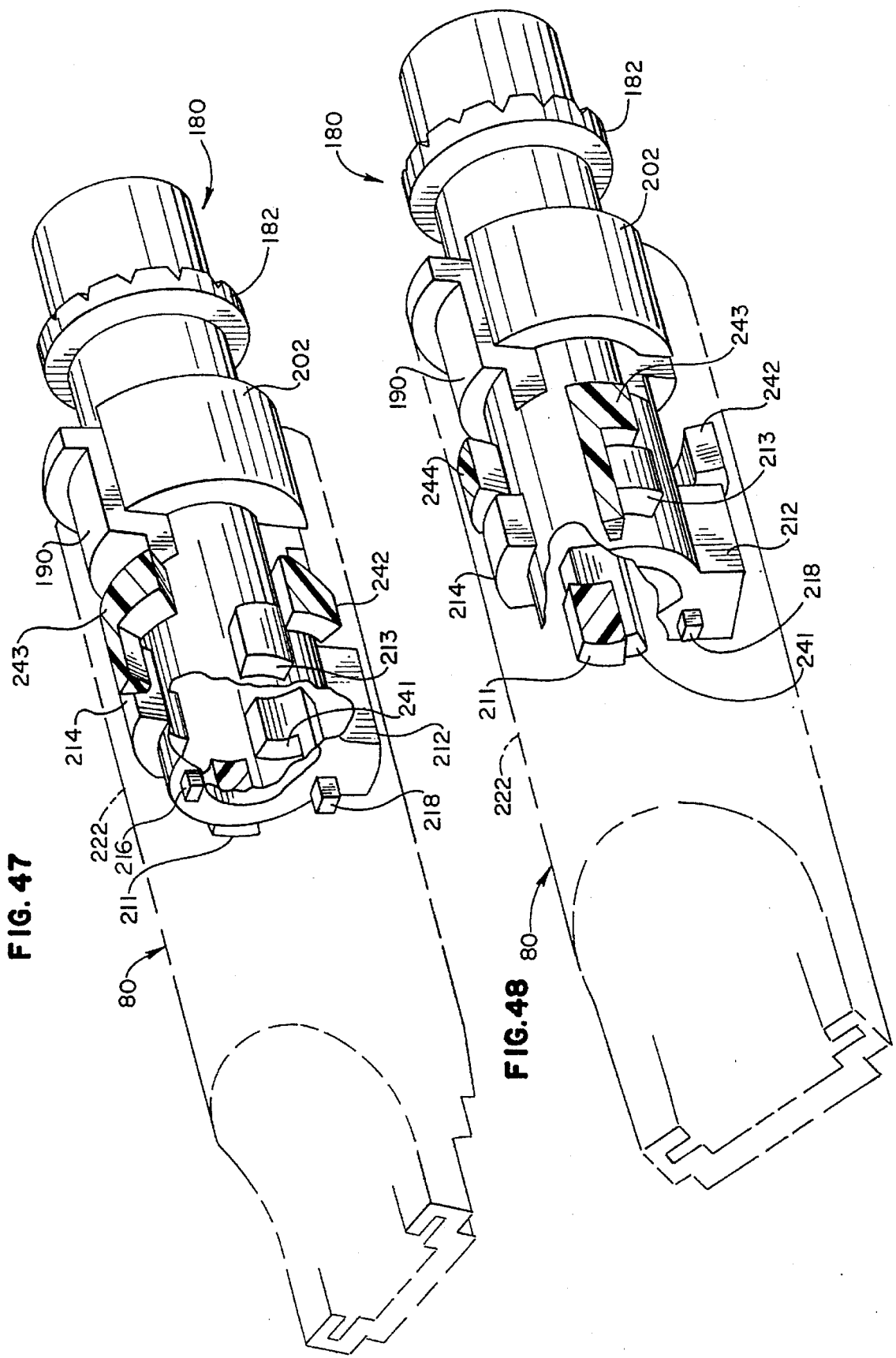

SURGICAL INSTRUMENT

CROSS-REFERENCE TO RELATED APPLICATIONS

This application is a division of prior application Ser. No. 08/259,322, filed Jun. 10, 1994, now U.S. Pat. No. 5,601,224, which is a continuation-in-part of application Ser. No. 07/959,184, filed Oct. 9, 1992, now U.S. Pat. No. 5,381,943, granted Jan. 17, 1995.

TECHNICAL FIELD

This invention relates generally to surgical instruments and is especially suitable for incorporation in various instruments, particularly staplers, used in endoscopic procedures as well as in open surgery procedures.

BACKGROUND OF THE INVENTION AND TECHNICAL PROBLEMS POSED BY THE PRIOR ART

A variety of designs have been commercialized or proposed for instruments which have an end effector for engaging tissue or other material during surgery and/or applying a fastener or other element to or through the material. Such instruments are typically actuatable from a handle, and some portions of the instrument may pivot and rotate to facilitate use of the instrument in various orientations. Examples of such instruments include tissue graspers, tissue clamps, needle graspers, tissue cutters, staplers, ligating clip appliers, and the like.

In many surgical procedures, the working area is confined, and instruments with relatively small cross sections are necessary or preferred. Thus, it would be desirable to provide improved assemblies that can be incorporated in a surgical instrument and that have relatively small cross sections.

In some surgical applications, it is necessary or advantageous to apply relatively high operating forces over particular portions of the instrument stroke length. Thus, it would be desirable to provide an improved actuator assembly that can provide a mechanical advantage for increasing the end effector force compared to the operator input force. It would also be beneficial if the actuator could accommodate designs wherein the operating force varies over the length of the stroke.

Additionally it would be advantageous to provide an improved assemblies that could be incorporated in instruments used in endoscopic surgical procedures as well as in instruments used in open surgery procedures. As used herein, the term "endoscopic" pertains generally to the use of a surgical instrument which is inserted into a body cavity in conjunction with an endoscope that is inserted into the same body cavity. The endoscope permits visual inspection, with or without magnification, of the interior of the body cavity and permits observation of the operation of the surgical instrument for therapeutic or diagnostic purposes.

In a typical endoscopic surgical procedure, the abdominal cavity of a human or animal subject is insufflated with a sterile gas, such as carbon dioxide, in order to provide increased maneuvering room within the body cavity for endoscopic instruments. Then, conventional trocars are inserted into the subject's body cavity through the surrounding skin, tissue, and musculature. A conventional trocar typically consists of a trocar cannula which houses an elongated trocar obturator. Trocar obturators typically have a piercing point, although other types of obturators are also available.

After each trocar has been positioned within the body cavity adjacent the target surgical site, the trocar obturator is removed leaving the trocar cannula as a pathway to the body cavity. A plurality of trocar cannulas are typically placed in this manner. The surgeon can then insert an endoscope through one of the trocar cannulas and can insert various types of endoscopic, surgical instruments through one or more of the other trocar cannulas at the target surgical site where the diagnostic or therapeutic surgical procedure is performed.

The endoscope is typically connected to a video camera, and the output from the video camera is fed to a video monitor which displays the surgical site and the end of the endoscopic instrument at the surgical site. Some endoscopic instruments incorporate a fastener-applying cartridge at the distal end which must be actuated. It would be desirable to provide an improved distal end assembly that can be employed in such endoscopic instruments and that can easily accommodate operation and control from the proximal end of the instrument exterior of the body cavity.

Although endoscopic surgical procedures offer many advantages, there are some problems associated with these procedures as conventionally practiced. For example, because the surgeon typically views the display on the video monitor as he manipulates instruments within the body cavity, the video display provides the surgeon with only a two-dimensional view of the surgical site, and there is a consequent loss of depth perception.

Another problem relates to engaging tissue from the instrument insertion direction. Some conventional, endoscopic instruments include an operable end effector (e.g., staple applying cartridge) for engaging the tissue in a certain way. In some of these conventional, endoscopic instruments, the end effectors are mounted to, and extend generally linearly with, a rigid, straight shaft of the instrument.

Depending upon the nature of the operation to be performed on the tissue within the body cavity, it may be desirable to provide an end effector assembly which can be easily rotated and/or angled or articulated relative to the longitudinal axis of the instrument shaft. This can permit the surgeon to more easily engage the tissue in some situations.

A further problem relates to the potential for blocking part of the field of view with the endoscopic instrument. Thus, the use of an endoscopic instrument with an articulating distal end would permit the surgeon to engage the tissue with an end effector laterally offset relative to the instrument's main shaft. This would permit the engaged tissue and instrument end effector to be better viewed through an adjacent endoscope with little or no interference from the main shaft.

Although a number of designs have been proposed for articulating endoscopic instruments, and although articulating endoscopes and other instruments are commercially available, it would be desirable to provide an improved design for a remotely operated end effector assembly that can accommodate articulation of the distal portion of the instrument.

In particular, it would be advantageous to provide an end effector assembly for an articulating instrument (endoscopic or non-endoscopic) with the capability for operation even when the assembly is oriented at a substantial oblique angle relative to the longitudinal axis of the instrument.

When an end effector is pivoted to an angled orientation relative to the longitudinal axis of the instrument, the mechanism for effecting the pivoting movement, depending upon the design of the mechanism, may require a greater applied force as the end effector approaches the maximum angle of divergence from the longitudinal axis. Accordingly, it would be advantageous to provide an improved system for pivoting an end effector with an increasing operating output force for an increasing pivot angle. Further, it would be beneficial if such an improved system could retain the desired angled orientation when the end effector is subjected to external forces and moments in the operating environment.

It would also be beneficial if such improved systems could be provided with sufficient strength to accommodate relatively high moments and forces during operation of the instrument in an articulated orientation as well as in a straight orientation.

It would also be advantageous if such improved systems for endoscopic or open surgery instruments could be provided with a relatively smooth exterior configuration having a minimum of indentations and projections that might serve as sites for contaminants and be hard to clean or that might be more likely to catch on, or tear, adjacent tissue.

Some instruments that are employed to apply fasteners are provided with a predetermined number of such fasteners. In some endoscopic instruments, such fasteners are stored in a cartridge at the distal end of the instrument. In some surgical procedures, it may be necessary to use more fasteners than can be stored in the instrument at one time. Accordingly, it would be desirable to provide an improved instrument for applying fasteners wherein additional fasteners can be added to the instrument. In particular, it would be advantageous if the empty fastener holder or cartridge could be removed and replaced with a new, full holder or cartridge.

Further, in order to minimize the likelihood that the cartridge could become inadvertently detached, it would be desirable to provide an improved system for latching the cartridge to the instrument.

Further, in order to facilitate attachment of a cartridge to an instrument, it would be beneficial to provide a system that would hold the interior components of the cartridge in position as the attachment connections to the instrument are being made.

In addition, it would be highly desirable to insure that the cartridge is properly installed on the instrument. To this end, it would be desirable to provide a loading or installation tool for assisting in the installation of the cartridge on the instrument in a way that would minimize the likelihood of an incomplete or improper installation.

It would be desirable in some applications to provide a fastener-containing cartridge that could rotate about its axis at the distal end of the instrument so as to facilitate positioning of the fastener in a desired orientation. Preferably, such cartridge rotation should be effected from the handle at the proximal end of the instrument.

While the rotational capability of the cartridge is highly desirable for this purpose, it would also be advantageous to provide means for preventing such rotation at certain times. In particular, it would be beneficial to provide a system for preventing cartridge rotation when external forces or moments are applied to the cartridge, as from contact with surrounding tissue or during installation of the cartridge.

Regardless of whether or not a fastener cartridge rotates at the distal end of an instrument, it would also be desirable in some applications to rotate the entire, elongate endoscopic shaft relative to the proximal handle of the instrument. It would be especially beneficial to provide the capability for effecting such shaft rotation from the proximal, handle portion of the instrument. This would permit orientation of the shaft to a particular rotated position that would be most convenient during a particular surgical procedure. However, once the shaft has been rotated to the selected position, it would be desirable to provide a system for maintaining the selected position. In particular, it would be desirable to provide an improved system for preventing rotation of the shaft when the shaft is subjected to forces and moments from surrounding tissue, or when a cartridge at the end of the shaft is separately rotated.

The present invention provides an improved jaw assembly for an instrument used in a surgical procedure which can accommodate designs having the above-discussed benefits and features.

SUMMARY OF THE INVENTION

The present invention includes a variety of aspects and features which may be incorporated altogether in a single instrument. On the other hand, the present invention contemplates that only one or some of the features may be incorporated in a particular instrument.

According to one aspect of the present invention, a trigger-actuating mechanism is provided for moving an end effector device (e.g., a staple former bar) in a surgical instrument between retracted and extended positions. The mechanism includes a frame which is integral with the instrument and which defines a guide channel. A trigger lever is pivotally mounted to the frame for rotation about a pivot axis offset from the frame guide channel. The trigger lever defines a cam channel offset from the pivot axis. A drive pin is disposed in the trigger cam channel and extends into the frame guide channel. A link is pivotally connected at a first location to the drive pin and is pivotally connected at a second location to the end effector device. A spring effectively acts between the frame and trigger lever to bias the trigger lever to an unactuated position in which the end effector device is at either the retracted or extended positions. In the preferred arrangement of this trigger actuating mechanism, an increased output force results near the end of the stroke along with a corresponding decrease in the end effector travel. This also provides an increased mechanical advantage in the portion of the actuating stroke and return stroke near the unactuated position. This permits a lower torque return spring to be used.

According to another aspect of the present invention, a control mechanism is provided for an articulating surgical instrument having a reciprocatable articulation driver member engaged with a pivoting portion that is pivotable between first and second positions in response to linear movement of the articulation driver member. The control mechanism moves the articulation driver member between extended and retracted positions within increased mechanical advantage at one of the extended and retracted positions. The control mechanism includes a frame integral with the instrument containing the articulation driver member. The articulation driver member includes a tooth. A helical gear is engaged with the tooth and is mounted for rotation on the frame. The helical gear has a decreasing pitch over at least a portion of its length so as to increase or decrease the mechanical advantage.

According to another aspect of the invention, a shaft rotation mechanism is provided for a surgical instrument that has a shaft which is carried in a frame and which is rotatable about a longitudinal axis relative to the frame. The shaft rotation mechanism incorporates a rotation control feature including a plurality of circumferentially spaced teeth defined in the frame along the longitudinal axis.

First and second arms extend outwardly from the shaft. Each arm has a deflection surface and an engaging surface. The deflection and engaging surfaces of the first arm are oriented oppositely relative to the deflection and engaging surfaces of the second arm. The engaging surface of the first arm is configured for engaging the teeth to prevent rotation of the shaft relative to the frame in a first direction. The engaging surface of the second arm is configured for engaging the teeth to prevent rotation of the shaft relative to the frame in second, opposite direction.

A knob is mounted on the frame for rotation relative to the frame about the longitudinal axis. The knob receives a proximal portion of the shaft and is engaged with the shaft to permit a predetermined lost motion angular displacement relative to the shaft in each of the first and second directions of rotation.

The knob includes a first cam surface for engaging and deflecting the first arm away from the teeth with the first cam surface when the knob is rotated in the first direction to the end of the range of the lost motion. The knob also includes a second cam surface, spaced from the first cam surface, for engaging and deflecting the second arm away from the teeth with the second cam surface when the knob is rotated in the second direction to the end of the range of the lost motion.

According to yet another aspect of the present invention, a system is provided for attaching a longitudinally rotatable cartridge of fasteners to a surgical fastener-applying instrument that includes a frame.

The system includes a holder on the frame fixed relative to the frame against longitudinal rotation. The holder defines an axially open receiving structure having a first engaging member. A proximal end of a rotatable carrier is retained axially in the holder receiving structure to accommodate longitudinal rotation relative to the holder and to accommodate limited axial movement between proximal and distal axial positions relative to the holder. The carrier has a proximally extending second engaging member for engaging the first engaging member to prevent carrier rotation only when the carrier is in its proximal axial position. The carrier also has at least one radially projecting lug.

The cartridge has an integral housing for being received on the carrier. The housing includes at least one radially projecting rib adapted to be disposed proximally of the carrier one lug. Axial movement of the housing onto the carrier with the rib angularly offset from the carrier lug moves the housing into a proximal position on the carrier and also urges the carrier to its proximal axial position in the holder receiving structure whereby its rotation relative to the holder receiving structure is prevented. The housing can then be rotated relative to the carrier so as to position at least a portion of the rib proximally of the lug with at least portions of the rib and lug having an axially aligned relationship to prevent axial withdrawal of the housing from the carrier.

Still another aspect of the present invention relates to a surgical instrument for applying a surgical fastener from a cartridge that can be releasably attached to a mounting portion of the instrument and that contains a reciprocatable fastener advancing member adapted to be driven from an actuator on the instrument. A system is provided for preventing longitudinal movement of the advancing member unless and until the cartridge is properly attached. The system includes a housing integral with the cartridge, and the housing defines a path for reciprocation of the advancing member while restraining the advancing member against rotation relative to the housing.

A longitudinal restraint member or washer is retained in the housing against longitudinal movement relative to the housing and is frictionally engaged with the housing to permit a relative angular displacement between the housing and the restraint member from a first angular orientation to a second angular orientation when a sufficient relative torque is applied between the restraint member and the housing.

The restraint member also defines a first anti-rotation engaging structure. This is adapted to engage a second anti-rotation engaging structure in the mounting portion of the instrument. The engagement of the two anti-rotation engaging structures prevents rotation of the restraint member relative to the mounting portion.

The advancing member and restraint member engage each other to prevent relative longitudinal movement when the housing and restraint member are in the first angular orientation. However, the advancing member and restraint member are disengaged in the second angular orientation. Thus, the cartridge can be attached to the mounting portion of the instrument by first moving the cartridge with the housing axially onto the mounting portions so as to effect engagement of the first and second anti-rotation engaging structures for restraining the restraint member against rotation. Subsequently, the housing is rotated relative to the restraint member from the first angular orientation to the second angular orientation to disengage the advancing member from the restraint member and thereby accommodate subsequent reciprocation of the member.

A still further aspect of the present invention provides an actuating system for use in an endoscopic surgical instrument that advances fasteners from a stored plurality of fasteners and wherein the instrument has (1) a frame, (2) an elongated tube mounted to the frame for rotation relative thereto, and (3) a structure or support pivotally mounted to the tube for movement to a pivoted position relative to the tube.

The actuating system includes a cartridge containing the fasteners and a reciprocatable advancing member in the cartridge for advancing the fasteners. The cartridge is mounted to the support for rotation relative thereto.

A dual function operating rod is engaged with the advancing member and extends to the frame. The rod includes a flexible portion to accommodate pivoting of the support. The rod is longitudinally reciprocatable to move the advancing member in the cartridge and is also rotatable to rotate the cartridge relative to the support.

An arcuate path-defining structure is present in either the tube or the support or both, and the arcuate path-defining structure receives the rod flexible portion. This establishes a frictional engagement that prevents rotation of the cartridge relative to the support when the cartridge is subjected to an externally applied torque that is less than a predetermined minimum torque. This frictional engagement is also substantially independent of the angle of articulation because the arcuate path-defining structure has a length that is substantially constant.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same, FIG. 1 is a simplified, perspective view of an instrument which includes the preferred combination of all of the features of the present invention;

FIG. 2 is a greatly enlarged, side elevational view of a staple that can be applied with the preferred embodiment of the instrument illustrated in FIG. 1, and the staple in FIG. 2 is shown in an open condition;

FIG. 3 is a view similar to FIG. 2, but FIG. 3 shows the staple after it has been applied by the instrument and deformed into the closed conditions;

FIG. 4 is a simplified, diagrammatic illustration of the process for advancing and applying the staples in the instrument;

FIG. 6 is a fragmentary, partial cross-sectional, exploded perspective view of the distal portion of the instrument shown in FIG. 1;

FIG. 7 is an enlarged, fragmentary, partial cross-sectional view of the instrument shown in FIG. 1 with portions of the instrument shown in phantom with dashed lines;

FIG. 7A is an enlarged, fragmentary, cross-sectional view taken generally along the planes 7A—7A in FIG. 7;

FIG. 7B is a fragmentary, side elevational view taken generally along the plane 7B—7B in FIG. 7A;

FIG. 7C is a fragmentary, cross-sectional view taken generally along the plane 7C—7C in FIG. 7;

FIG. 7D is a view similar to FIG. 7B, but FIG. 7D shows an alternate embodiment of the trigger lever cam channel;

FIG. 7E is a view similar to FIG. 7, but FIG. 7E shows the alternate embodiment of the trigger lever cam channel;

FIG. 8 is a view similar to FIG. 7, but FIG. 8 shows the instrument in an actuated position with the trigger lever squeezed completely to the end of its travel;

FIG. 9 is a view similar to FIG. 7, but FIG. 9 shows in detail the mechanism for effecting articulation of the instrument;

FIG. 9A is a cross-sectional view taken generally along the plane 9A—9A in FIG. 9;

FIG. 10 is a fragmentary, partial cross-sectional view of the components in the instrument which effect rotation of the cartridge at the distal end of the instrument;

FIG. 11 is an enlarged, fragmentary, partial cross-sectional view of the distal end of the instrument, and FIG. 11 illustrates in more detail the arrangement of the components for effecting rotation of the cartridge;

FIG. 12 is an enlarged, fragmentary, perspective, partial cross-sectional view of the shaft and shaft rotation knob as viewed from the proximal end of the instrument;

FIG. 12A is a greatly enlarged, fragmentary, partial cross-sectional view taken generally along the plane 12A—12A in FIG. 12;

FIG. 13 is an enlarged, fragmentary, perspective, partial cross-sectional view of the instrument handle portion and shaft mounted therein as viewed from the distal end of the instrument;

FIG. 14 is a greatly enlarged, cross-sectional view taken generally along the plane 14—14 in FIG. 12;

FIG. 15 is an enlarged, partial cross-sectional view taken generally along the plane 15—15 in FIG. 13;

FIG. 16 is an enlarged, exploded perspective view of the cartridge which is attached to the distal end of the instrument shown in FIG. 1;

FIG. 17 is an enlarged, fragmentary, partial cross-sectional view of the distal end of the instrument shown in FIG. 1;

FIG. 17A is a fragmentary, exploded perspective view of the proximal portion of the staple former plate and receiving operating rod connector;

FIG. 17B is a fragmentary, cross-sectional view taken generally along the plane 17B—17B;

FIG. 18 is a fragmentary, cross-sectional view taken generally along the plane 18—18 in FIG. 17;

FIGS. 19-25 are cross-sectional views taken generally along the planes 19-25, respectively in FIG. 18;

FIGS. 26-30 are greatly enlarged views similar to FIG. 19 showing the distal end of the cartridge and illustrating the operational sequence of the application of a staple;

FIG. 31 is a simplified, partially diagrammatic, fragmentary, perspective view of a loading sleeve adapted to engage the cartridge housing of the instrument shown in FIG. 1, and FIG. 31 shows the housing prior to being mounted on the carrier, it being understood that the internal cartridge components and internal carrier components have been omitted for ease of illustrations;

FIG. 32 is a greatly enlarged, end elevational view taken generally along the plane 32—32 in FIG. 31;

FIG. 33 is a view similar to FIG. 31, but FIG. 33 shows the components in an intermediate assembly stage;

FIG. 34 is a greatly enlarged, cross-sectional view taken generally along the plane 34—34 in FIG. 33;

FIG. 35 is a view similar to FIG. 33, but FIG. 35 shows the components in a later stage of assembly;

FIG. 36 is a greatly enlarged, cross-sectional view taken generally along the plane 36—36 in FIG. 35;

FIG. 37 is an enlarged, perspective view of the cartridge of the present invention with portions cut away to illustrate interior detail and with portions of the internal components omitted for ease of illustration;

FIG. 38 is a cross-sectional view similar to FIG. 17, but FIG. 38 shows the components in a preliminary orientation prior to being arranged in a final, operable orientation that is illustrated in FIG. 17;

FIG. 39 is a cross-sectional view taken generally along the plane 39—39 in FIG. 38;

FIG. 40 is a view similar to FIG. 39, but FIG. 39 shows a moved position of the cartridge relative to the retainer washer;

FIG. 41 is a view similar to FIG. 35, but FIG. 41 shows the arrangement of the components at a later stage of assembly;

FIG. 42 is a greatly enlarged, cross-sectional view taken generally along the plane 42—42 in FIG. 41;

FIG. 43 is a view similar to FIG. 41, but FIG. 43 shows a later stage in the assembly process as the loading sleeve is being withdrawn;

FIG. 44 is a greatly enlarged, fragmentary, cross-sectional view taken generally along the plane 44—44 in FIG. 41;

FIG. 45 is a fragmentary, cross-sectional view taken generally along the plane 45—45 in FIG. 44;

FIG. 46 is a greatly enlarged, cross-sectional view taken generally along the plane 46—46 in FIG. 43;

FIG. 47 is an enlarged perspective view of the cartridge and carrier engaged in an intermediate position with the cartridge shown partially in phantom and with portions broken away to illustrate interior detail; and FIG. 48 is a view similar to FIG. 47, but FIG. 48 shows the components fully assembled in the locked, operable orientation.

DESCRIPTION OF THE PREFERRED EMBODIMENTS

Figure 5:
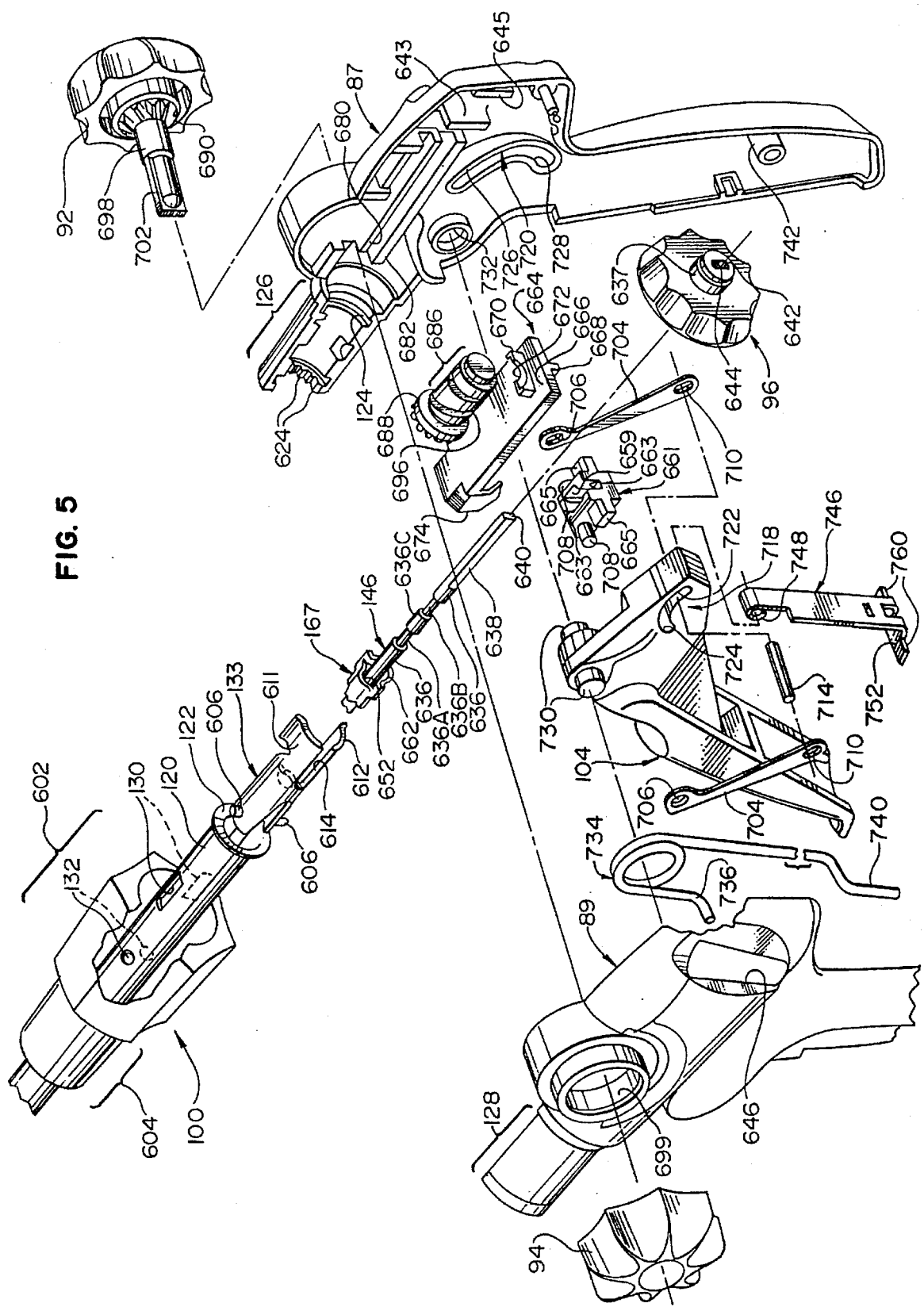
FIG. 5 is a fragmentary, partial cross-sectional, exploded perspective view of the proximal portion of the instrument shown in FIG. 1.

While this invention is susceptible of embodiment in many different forms, this specification and the accompanying drawings disclose only one specific form as an example of the invention. The invention is not intended to be limited to the embodiment so described, however. The scope of the invention is pointed out in the appended claims.

For ease of description, components of this invention are described in various operating positions, and terms such as upper, lower, horizontal, etc., are used with reference to these positions. It will be understood, however, that components and assemblies incorporating features of this invention may be manufactured, stored, transported, used, and sold in an orientation other than the position described.

Some of the figures illustrating aspects of the invention show some mechanical elements that are known and that will be recognized by one skilled in the art. The detailed descriptions of such elements are not necessary to an understanding of the invention, and accordingly, are herein presented only to the degree necessary to facilitate an understanding of the novel features of the present invention.

Further, various assemblies and subassemblies incorporating aspects of the present invention can be used in instruments that have certain conventional assemblies or components the details of which, although not fully illustrated or described, will be apparent to those having skill in the art and an understanding of the necessary functions of such assemblies or components.

INTRODUCTION

The present invention includes a number of features which may be incorporated together in a preferred embodiment of an endoscopic surgical stapler. However, according to the principles of the present invention, only one or some of the features may be included in a surgical stapler or in other types of surgical instruments, such as ligating clip appliers, graspers, and the like.

The general arrangement and operation of the preferred embodiment of an endoscopic surgical stapler is briefly described in the immediately following section entitled "General Arrangement and Operation of The Instrument." Succeeding sections are directed to specific portions or features of the instrument.

GENERAL ARRANGEMENT AND OPERATION OF THE INSTRUMENT

Referring to FIG. 1, a preferred embodiment of an endoscopic surgical stapler is designated generally by the reference numeral 50. The stapler 50 is adapted to hold a supply of staples 52 (FIGS. 2, 3, and 4) and to apply the staples 52 to tissue (not shown).

The staples 52 may be employed to hold two portions of tissue together. If desired, the staples 52 may also be employed to attach a non-tissue element (e.g., a medical implant device, surgical mesh, etc.) to one or more portions of tissue. The staple 52 is made from a suitable material, such as titanium, stainless steel, or the like. In appropriate applications, nonmetallic materials, including synthetic polymers, may be employed.

As described in detail hereinafter, one of the features of the preferred embodiment of the stapler 50 relates to a novel mechanism for advancing and applying the staples which have a unique configuration, such as the staples 52. In particular, each staple 52 has a transverse member or crown 54 which has two end portions 56 joined by a central portion 58. The central portion 58 has an upwardly convex configuration defining a hump rising above the two crown end portions 56. Each crown end portion 56 merges with a leg 60 that is oriented generally perpendicular to the crown 54 and that has an angled distal end surface 62 which defines a piercing point.

The staples 52 are advanced by the instrument by the stapler 50 and applied to tissue in a novel manner described in detail hereinafter. Briefly, however, each staple 52 is pushed with the instrument 50 into tissue so that the points of the legs 60 penetrate the tissue (or penetrate an auxiliary element (e.g., mesh) along with the tissue). Depending on the selected design parameters, the staple legs 60 may be advanced into the tissue to a predetermined depth. In some applications, it may be desirable to advance the legs 60 into the tissue to the greatest depth possible—until the staple crown 54 is in sufficient compressive engagement with the tissue and/or auxiliary element being stapled to the tissue.

Subsequently, the stapler 50 deforms the staple crown 54 (as described in more detail hereinafter) so that the staple legs 60 assume a generally closed orientation as illustrated in FIG. 3. Preferably, the distal ends of the staple leg 60 overlap somewhat as shown in FIG. 3.

In the preferred embodiment of the stapler 50, the staples 52 are stored in a stacked array as illustrated in FIG. 4. The staples 52 are oriented in a side-by-side stacked array which is biased forwardly toward the distal end of the instrument along a longitudinal direction generally identified by the arrow 64 in FIG. 4. The staples 52 are oriented in the stacked array so that the staple legs 60 point generally perpendicularly relative to the longitudinal direction 64. The stacked array of staples 52 is biased in the direction indicated by the arrow 64 by a helical compression spring 66 which forces an engaging member or tab 68 against the most proximal staple in the array.

When the instrument 50 is operated to apply a staple, the lead staple at the front end or distal end of the array of staples is moved down an angled path (as schematically illustrated by arrow 69 in FIG. 4) and is rotated about 90 degrees (by means described in detail hereinafter) to the position generally indicated for the staple 52B in FIG. 4. In this position, the staple legs 60 now point distally along the direction indicated by the arrow 64. The re-orientation of the staple 52B is effected in conjunction with a cooperative guiding of the staple in a guide track (not shown in FIG. 4, but described hereinafter) and by engagement with the distal ends 70 of a staple former (described in more detail hereinafter). This effects advancement of the staple 52B to the distal end of the stapler 50 where the staple legs 60 penetrate the tissue and where the staple crown 54 is bent around the arms or prongs 72 of an anvil so that the staple legs close as illustrated in FIG. 4 for a previously closed staple 52C.

The staples 52 are stored adjacent the distal end of the stapler 50 in a cartridge 80 which is mounted at the end of the stapler 50. With reference to FIG. 1, the cartridge 80 defines the distal portion of an elongate, tubular portion or shaft 84 extending from a proximal housing, frame, or handle 86. The transverse cross section of the shaft 84 has a generally circular peripheral configuration except at the distal end of the cartridge 80 which has a somewhat tapered, non-circular configuration described in more detail hereinafter. Typically, the maximum outside diameter of the shaft 84 is sized to fit through a conventional trocar. In the embodiment illustrated, the maximum outside diameter is about 10.9 mm (0.43 inch).

A distal portion of the shaft 84 which carries the cartridge 80 pivots about a transverse axis 90. The stapler can thus articulate to move the distal portion away from a position generally in line with the stapler longitudinal axis 82 (which in-line position is shown in solid lines in FIG. 1). The shaft distal portion can be pivoted to a position at an angle relative to the longitudinal axis 82 (which pivoted position is shown in phantom by dashed lines in FIG. 1).

The distal end of the stapler 50 can be articulated with controls at the proximal end of the stapler by mechanisms described in detail hereinafter. The pivoting or articulation of the cartridge 80 can be effected with such mechanisms by rotation of either of two knobs 92 or 94 on the handle 86 in a manner described in detail hereinafter.

The cartridge 80 can also rotate about the longitudinal axis 82 relative to the rest of the tubular shaft 84 as indicated by the double headed arrow 95 in FIG. 1, and this can be effected by rotation of a knob 96 at the proximal end of the stapler handle 86 as explained in more detail hereinafter.

Additionally, the entire tubular shaft 84, including the cartridge 80, can be rotated relative to the handle 86 about the longitudinal axis 82 as indicated by the double-headed arrow 98 in FIG. 1. The shaft rotation is effected at the handle 86 by rotating a knob 100 that is mounted on the handle 86 and that is engaged with the tubular portion 84.

Also, as described in detail hereinafter, the cartridge 80 is removable from the distal end of the stapler 50 so that when all of the staples initially supplied in the cartridge 80 have been applied to tissue, the empty cartridge may be removed from the stapler 50, and a new cartridge full of staples may be installed on the stapler 50. A novel cartridge loading tool may be employed to facilitate the installation process. The structures which accommodate this process are described in detail hereinafter.

The staples 52 are advanced and applied to tissue by squeezing a trigger lever 104 on the handle 86. The trigger lever 104 is pivotally mounted to the handle 86 for movement in the proximal direction and in the distal direction as indicated by the double-headed arrow 108 in FIG. 1. The housing, frame, or handle 86 includes a downwardly depending handle grip 112 which can be held in the palm of the hand while the fingers of the hand extend around the trigger lever 104 so as to squeeze the trigger lever 104 proximally toward the handle grip 112. The housing, frame, or handle 86 includes two, mating handle sections 87 and 89 which contain and support interior components and exterior components as described in detail hereinafter.

The components of the stapler 50 may be fabricated from suitable materials. It is presently contemplated that some of the components, such as the knobs 92, 94, 96, and 100, as well as the other handle components, such as the trigger lever 104 and handle grip 112, would be fabricated from synthetic polymers, such as polycarbonate, nylon, and the like. Other, alternative materials may be employed. For some of the other components, especially components that transfer internal forces and moments, metallic materials may be employed (e.g., steel, stainless steel, etc.).

THE SUPPORT TUBE

The elongate, endoscopic portion or shaft 84 includes a generally cylindrical, hollow support tube 120 as shown in FIGS. 1, 5, and 6. The proximal end of the tube 120 has a radially extending flange 122 (FIG. 5), and the flange 122 is received in an annular groove 124 (FIG. 5) defined in the handle sections 87 and 89. The annular groove is defined in a distally extending neck section 126 of the handle section 87 and in a mating neck section 128 at the distal end of the handle section 89.

The tube 120 is mounted within the neck sections 126 and 128 and extends distally therefrom. The tube 120 defines a pair of slots 130 adjacent the proximal end of the tube 120 (FIGS. 5, 12, and 13). The slots 130 are about 120 degrees apart and are located within the neck portions 126 and 128 of the handle sections. Near the slots 130, the tube 120 defines a pair of apertures 132 which are about 180 degrees apart. The apertures 132 and the slots 130 accommodate an internal driver 133, described in detail hereinafter, which controls the rotation, and rotational position, of the tube 120 about the longitudinal axis 82 relative to the handle 86.

In a presently contemplated embodiment, the tube is about 12 inches long, has an internal diameter of about 10.4 mm (0.41 inch), has an outside diameter of about 10.9 mm (0.43 inch), has a wall thickness of about 0.254 mm (0.01 inch), and is fabricated from metal, such as steel.

THE PIVOT HOUSINGS, PIVOTAL SHELLS, AND ARTICULATION DRIVER

The distal end of the tube 120 is crimped to a pair of pivot housings 134 and 136 (FIGS. 1 and 6). As illustrated for the pivot housing 134 in FIG. 11, the proximal portion of each pivot housing extends inwardly into the tube 120. The tube 120 is secured to each housing by a pair of inwardly deformed dimples 138 (FIGS. 1, 7, and 11). The exterior of each pivot housing 134 and 136 has circular recesses or cavities, such as the recess 140 shown in the pivot housing 136 in FIG. 6, for receiving the tube dimples. The pivot housings 134 and 136 thus are secured in mating relationship to the tube 120 and extend therefrom.

The inside of the pivot housing 134 defines an arcuate channel 142 (FIGS. 6 and 11) for accommodating a portion of a flexible cable 144 which is part of a dual function operating rod 146 (FIG. 11). The rod 146 is operable from the handle 86 to (1) advance and apply the staples 52 and (2) effect rotation of the staple cartridge 80 relative to the tube 120 while at the same time accommodate the pivoting or articulation of the distal end of the stapler shaft 84. The operating rod 146, and mechanisms for effecting its operation, are described in more detail hereinafter.

The distal end of the pivot housing 134 has a lug 148 defining a bore 150, and the distal end of the pivot housing 136 has a lug 152 defining a bore 154 (FIG. 6). The bores 150 and 154 are aligned transversely and define the pivot axis or articulation axis 90 (FIG. 1) about which the distal end of the stapler pivots or articulates.

As illustrated in FIG. 6, a pair of pivotal shells 156 and 158 are pivotally mounted to the pivot housings 134 and 136, respectively. The shells 156 and 158 function as a support or holder for components at the distal end of the stapler as described in detail hereinafter. The proximal end of the pivotal shell 156 has an outwardly projecting pin 160 for being received in the bore 150 of the pivot housing 134, and the shell 158 has an outwardly projecting pin 162 for being received in the bore 154 of the pivot housing 136.

The shell 158 includes an inwardly projecting pin 164, and the shell 156 defines a bore 166 for receiving the distal end of the pin 164. The pin 164 also passes through an arcuate channel 165 in the distal end of an articulation driver rod or plate 167 which extends from the handle 86 and which is described in more detail hereinafter.

The distal end of the shell 156 includes a flange 168, and the distal end of the shell 158 includes a flange 170. A cylindrical sleeve 172 fits over the cylindrical shape defined by the shells 156 and 158 when the shells 156 and 158 are in an assembled, mating relationship as shown in FIGS. 1, 7, 11, 17, and 18. The sleeve 172 abuts the shell flanges 168 and 170.

The inside of the pivotal shell 156 defines an arcuate channel 174 as illustrated in FIGS. 6 and 11 for receiving a portion of the flexible cable 144. The proximal end of the channel 174 flares outwardly as at 176 and 178 to accommodate pivoting of the shell 156 (together with shell 158) relative to the pivot housings 156 and 136 without the proximal end of the channel 174 cutting into the cable 144.

The shells 156 and 158 can be pivoted to carry with them the projecting distal end portion of the stapler. This is effected by movement of the articulation driver plate 167 along the longitudinal axis (axis 82) in FIGS. 1 and 9. When the driver plate 167 is in the extended position (as shown in phantom in dashed lines in FIG. 9) the pin 164 of the shell 158 is at the bottom, proximal end of the cam channel 165. In this position, the distal end of the stapler is generally in line with the longitudinal axis 82 of the non-articulating portion of the shaft 84.

When the articulation driver member 167 is retracted (by means described in detail hereinafter) to the position shown in solid lines in FIG. 9, the cam channel 165 forces the shell pin 164 upwardly so as to pivot the distal end of the stapler.

Preferably, the peripheral sidewalls at the distal ends at the pivot housing 134 and 136 and the sidewalls at the proximal ends at the shells 156 and 158 are configured as necessary to permit the desired range of motion. Preferably, at the end of the desired range of motion, portions of the adjacent ends or edges of the housings and shells engage to provide a mechanical stop.

In the preferred embodiment illustrated, the distal end of the stapler 50 can be articulated through an angle up to about 60 degrees. In some applications, it may be desirable to provide a greater articulation angle. In general, large articulation angles are not required owing to the capability for rotating the shaft portion 84 about the longitudinal axis 82 (as indicated by the double-headed arrow 98 in FIG. 1). The combination of the articulation of the shaft distal end to a selected angle and the angular displacement of the shaft (with the cartridge 80 carried thereon) provides a wide range of movement which permits the application of staples at a large number of locations in a variety of orientations of the stapler.

THE ROTATABLE CARTRIDGE MOUNTING MECHANISM

As illustrated in FIGS. 6, 11, 17, 18, 31, and 41, a mounting portion or member, in the form of a rotatable carrier or swivel idler 180, is employed to mount the cartridge 80 to the pivotal shells 156 and 158. The swivel idler 180 has a generally cylindrical configuration with a radial flange 182 spaced distally of its proximal end. The flange 182 is received in a groove 184 defined in the inside of the shells 156 and 158 (FIGS. 6, 17, 18, 41, 44, and 45).

Each shell 156 and 158 has an inwardly projecting tooth 186 which projects distally from the proximal side of the groove 184 as illustrated for the shell 156 in FIG. 45. With reference to FIGS. 41 and 45, the idler flange 182 defines a plurality of proximally facing, circumferentially spaced notches 188. Each notch 188 is adapted to receive and engage one of the two teeth 186 when proper angular alignment is established between the teeth and notches.

It will be noted, however, that the groove 184 in the shells 156 and 158 is wider than the axial dimension (i.e., thickness) of the idler flange 182 by an amount at least equal to the depth of the notches 188. Thus, if the idler 180 is disposed in its most distal position (as shown in FIGS. 17, 18, and 38), then the idler flange notches 188 will not be able to receive and engage the shell teeth 186, and the idler 180 will thus be free to rotate about the shaft longitudinal axis within the shells 156 and 158. However, if an axial force is applied to the distal end of the stapler, the swivel idler 180 will move proximally so that the idler flange notches 188 engage the shell teeth 186. This would prevent relative rotation between the swivel idler 180 and cartridge 80 mounted thereon on the one hand and the shells 156 and 158 on the other hand.

When there is no substantial axial force urging the swivel idler 180 proximally, the swivel idler 180 can be rotated relative to the shells 156 and 158. The shape of the idler flange notches 188 and of the mating shell teeth 186 permits rotation of the idler 180 unless a sufficient axial force is applied to the idler 180.

The above-described engaging notch and tooth structure of the idler and shells prevents the idler 180 and cartridge 80 from rotating during application of a staple into tissue. The rotational restraint of the cartridge by the notch/tooth engagement also occurs during initial installation of the cartridge 80 onto the idler 180 as explained in detail hereinafter, and this significantly facilitates the assembly process.

As illustrated in FIGS. 31 and 33, the swivel idler 180 is hollow and has an interior passage with a generally D-shaped transverse cross section which, as best seen in FIG. 36, defines a partially cylindrical interior surface 192 and a planar surface 194. The passage is adapted to receive a connector 196 attached to the end of the flexible cable 144 as illustrated in FIGS. 6, 17, 17A, 17B, and 38. As best illustrated in FIG. 17A, the connector 196 has a generally D-shaped exterior configuration, and as illustrated in FIGS. 17 and 18, the connector 196 is received within the proximal end of the passage in the swivel idler 180.

As illustrated in FIG. 31, the swivel idler 180 includes a central, wide flange 198 which extends partway around the circumference of the swivel idler 180. A narrow flange 200 projects from the wide flange 198. The wide flange 198 and narrow flange 200 are separated by a slot from a deflectable flange section 202 which is connected with a narrow neck section 204 to a reduced diameter, cylindrical, distal end portion 206. In the unstressed condition, the deflectable flange section 202 extends radially outwardly further than the adjacent wide flange 198. The deflectable flange section 202 can be pushed radially inwardly to a radius equal to or less than the radius of the wide flange 198. The flange section 202 functions, as explained in more detail hereinafter, to releasably retain the cartridge 80 on the swivel idler 180.

The distal end portion 206 of the swivel idler includes four outwardly projecting lugs 211, 212, 213, and 214 as illustrated in FIG. 31. The centers of the lugs 212 and 214 are about 180 degrees apart. The centers of the lugs 211 and 213 are about 180 degrees apart. The lugs 211 and 213 are not exactly equally spaced between the lugs 212 and 214. The lug 213 is closer to the lug 214 than to the lug 212. The lug 211 is closer to the lug 212 than to the lug 214.

The lug 212 is wider than the other three lugs (as measured around the idler circumference). The lug 214 is not as wide as the lug 212, but the lug 214 is wider than the lugs 211 and 213. The lugs 211 and 213 have approximately the same width.

All of the lugs 211, 212, 213, 214 terminate in the proximal direction at the same longitudinal location along the longitudinal axis of the swivel idler 180. The lugs 211, 213, and 214 all terminate in the distal direction at the same longitudinal location relative to the longitudinal axis of the swivel idler 180. In particular, the distal end face of each lug 211, 213, and 214 is set back proximally from the distal end of the idler 180 by the same distance. On the other hand, the lug 212 extends all the way to the distal end of the idler 180.

The lugs 211, 212, 213, and 214 function as a keying system to assist in the proper installation of the cartridge 80 onto the idler 180 as described in detail hereinafter. In addition, the lugs 211, 212, 213, and 214 serve to assist in retaining the cartridge 180 on the swivel idler 180 and also serve to assist in removal of a special cartridge loading tool that can be employed to install the cartridge as described in detail hereinafter.

On the distal end face of the swivel idler 180, there are two, axially projecting lugs 216 and 218 as illustrated in FIG. 31. The lugs 216 and 218 are adapted to engage a retainer washer 220 mounted within the cartridge 80 as illustrated in FIGS. 16, 18, 23, and 37–40 and explained in more detail hereinafter.

THE CARTRIDGE HOUSING AND INTERNAL COMPONENTS

The cartridge 80 includes a generally hollow housing 222 containing internal components for storing, advancing, and applying the staples 52 as illustrated in FIG. 16. Preferably, the housing 222 is molded from a generally transparent, thermoplastic material, such as a polycarbonate polymer.

As illustrated in FIG. 31, the cartridge housing 222 defines four rectangular apertures or windows 231, 232, 233, and 234. The windows 231 and 234 are the same size but are narrower than the windows 232 and 234. The windows 232 and 234 are the same size. The windows 231 and 233 each have a small rectangular notch 235 at one corner at the distal end of the window.

When properly installed (as by a process described in detail hereinafter), the windows 231, 232, 233, and 234 are disposed adjacent the swivel idler lugs 211, 212, 213, and 214, respectively.

As illustrated in FIGS. 31, 32, and 37, the inside of the cartridge housing 222 includes two L-shaped lugs or ribs 241 and 243 associated with the windows 231 and 233, respectively. As shown in FIGS. 31 and 37 for the lug 241 at the window 231, each L-shaped lug extends along the proximal edge of the window and also along one longitudinal side of the window. The lug terminates short of the distal end of the window at the notch 235 (FIG. 37) for engaging a retainer washer 220 described in more detail hereinafter.

Also, as shown in FIG. 32, the inside of the cartridge housing defines two ribs 242 and 244 at the proximal ends of the windows 232 and 234, respectively. Ribs 242 and 244 are similar to the ribs 241 and 243 except that neither rib 242 or 244 has a portion extending longitudinally along a longitudinal side of the associated window.

The cartridge ribs 241, 242, 243, and 244 cooperate with the swivel idler lugs 211, 212, 213, and 214, respectively, and function during installation of the cartridge as a keying system to establish proper cartridge orientation. The ribs and lugs also function after installation as a retention system for preventing removal of the cartridge housing 222 from the idler 180. To this end, when the cartridge housing 222 is properly mounted on the swivel idler 180, the foot portions of the L-shaped ribs 241 and 243 in the cartridge engage the proximal ends of the associated swivel idler lugs 211 and 213, respectively, and the cartridge ribs 242 and 244 engage the proximal ends of the associated swivel idler lugs 212 and 214 so as to prevent the cartridge housing 222 from being directly pulled off of the idler 180.

As illustrated in FIGS. 31 and 37, the cartridge housing 222 also defines a large notch 250 at its proximal end. When the cartridge housing 222 is properly installed on the swivel idler 180, the notch 250 receives the swivel idler deflectable flange section 202. The deflectable flange section 202 is relatively thick. In the undeflected position, the flange section 202 extends radially outwardly beyond the periphery of the adjacent idler flange 198. In this undeflected position, the flange 202 projects into the cartridge housing notch 250. This helps lock the cartridge housing 222 in the desired rotational position on the swivel idler 180.

The cartridge housing 222 defines a novel, internal structure for holding the staples 52 and the associated internal components as illustrated in FIGS. 16–25. The cartridge housing 222 has a tapered nose 260 (FIGS. 16 and 18) which has an internal slot or track 262 (FIG. 19) which opens to the distal end of the instrument. The slot 262 is adapted to receive the legs of a horizontally oriented staple 52 as the staple 52 is advanced through the nose 260.

The proximal end of the slot 262 opens to another slot or track 264 (FIG. 21) which is higher than the slot 262 so as to accommodate to legs 60 of the vertically oriented staples in the stacked array. Below the slot 264, an interior length of the cartridge extending proximally from the nose 260 is defined as shown in FIG. 21 by a pair spaced-apart angled surfaces 266, by inwardly projecting ledges 268, and by an undercut slot 270. As shown in FIG. 21, the interior volume defined by the slot 264, surfaces 266, ledges 268, and slot 270 accommodate an inserted staple track member 274. The staple track member 274, which is shown in a perspective view in FIGS. 16 and 16B, supports the stacked array of staples 52.

The staple track member 274 has a foot 276 (FIG. 18) which extends laterally on each side, as shown in FIG. 22 into the cartridge bottom slot 270 under the ledges 268.

With reference to FIG. 18, a space 278 between the bottom of the distal portion of the staple track member 274 and the cartridge housing accommodates the proximal end 280 of an ejector spring 282. As shown in the perspective view in FIG. 16, the ejector spring 282 includes an upwardly angled portion 284 extending from the proximal end portion 280, a vertical portion 285 extending from the angled portion 284, and a pair of distally projecting, but upwardly angled, spring arms 286.

Figure 16A:
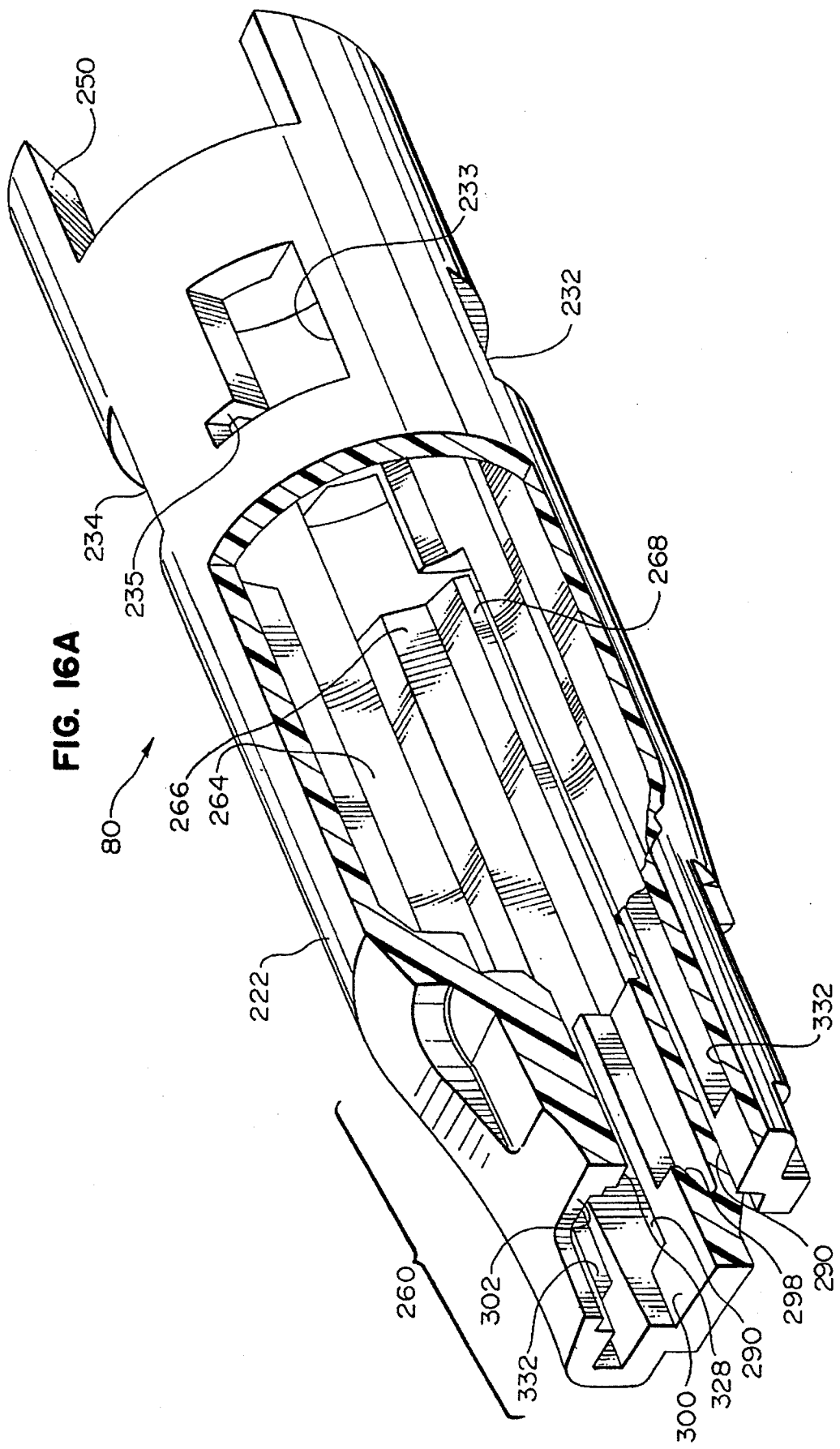
FIG. 16A is a greatly enlarged, perspective view of the housing of the cartridge shown in FIG. 16 with portions of the housing cut away to illustrate interior detail and with interior components omitted for clarity.
Figure 16B:
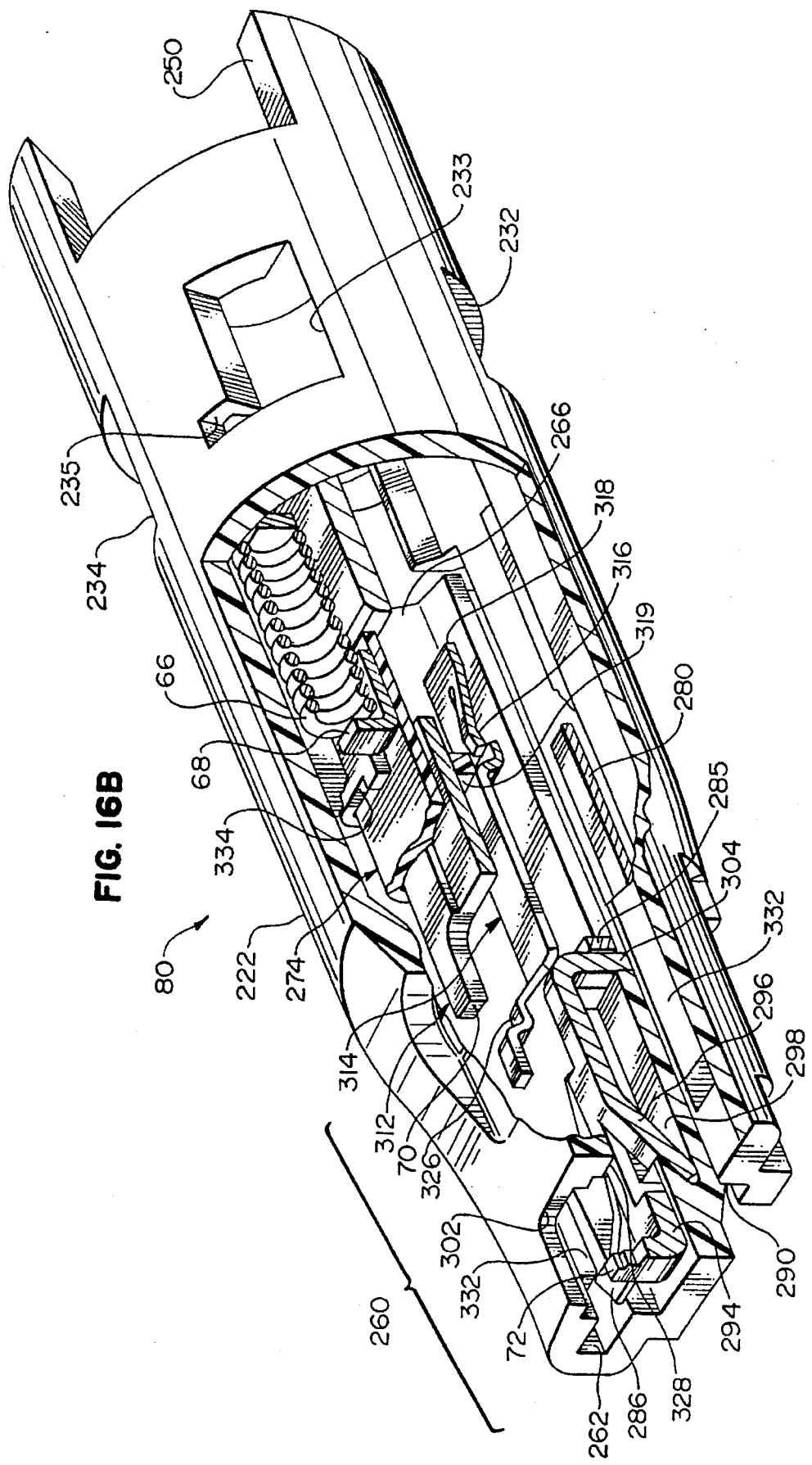
FIG. 16B is a view similar to FIG. 16A, but FIG. 16B shows some of the interior components in place.

As shown in FIGS. 16A, 16B, and 18, the spring arms 286 are accommodated in a pair of spaced-apart slots 290 below the staple track 262.

An anvil 292 (FIGS. 16 and 26) is disposed in the front of the cartridge housing 222. The anvil 292 has a plate 294 with a downwardly angled retaining tab 296 (as shown in FIGS. 18 and 26). The tab 296 is received in a slot 298 defined in the middle of the cartridge housing 222 adjacent the distal end. The slot 298 opens to a platform or surface 300 (FIGS. 16A, 16B, and 18) on which the anvil plate 294 is disposed. The previously identified pair of anvil prongs 72 project upwardly from the distal end of the anvil plate 294. The distal end of the upper side of the cartridge housing 222 is provided with a cut-out or notch 302 to accommodate the anvil prongs 72 and the adjacent distal ends of the spring arms 286 as shown in FIGS. 16B and 18.

The proximal end of the anvil 292 defines a downwardly projecting portion 304 as shown in FIG. 16. As shown in FIGS. 16B and 18, the downwardly extending portion 304 is disposed adjacent, but distally of, the ejector spring vertical portion 185.

As shown in FIGS. 16 and 21, the staple track member 274 defines a central, longitudinally oriented, component receiving passage having a narrow middle region 306, a lower wide region 308, and an upper wide region 310. As illustrated in FIG. 21, the upper wide region 310 receives a former bar or plate 312, and the lower wide region 308 receives a pickup spring 314.

As illustrated in FIG. 18, the pickup spring 314 has proximal end plate portion 316 with an upwardly angled tab 318. The tab 318 terminates at its distal end adjacent an internal retention lug 319 in the staple track member 274.

The distal end of the pickup spring plate portion 316 includes a pair of spring arms each having an upwardly extending portion 320, a longitudinally extending portion 322, and an upwardly angled distal end portion 324 which defines a staple receiving cradle 326. As shown in FIG. 18, the upwardly angled distal end portion 324 of each arm of the pickup spring 314 extends distally beyond the distal end of the staple track member 274. The pickup spring arm distal end portions 324 straddle a rib 328, as shown in FIGS. 20 and 26, which depends downwardly from the cartridge housing 222.

The former plate distal ends 70 are spaced apart by a distance sufficient to pass along the outside edges of the pickup spring arm cradles 326 as can be seen in FIG. 17. The distal end of the staple former plate 312 defines a longitudinal channel 330 (FIG. 16) for accommodating the cartridge housing rib 328 when the former plate 312 is moved distally to advance a staple.

As illustrated in FIGS. 16B and 20, the proximal portion of the staple track 262 in the cartridge housing nose 260 is adjacent a pair of vertical slots 332 which are open to the bottom of the cartridge housing 222. The vertical slots 332 accommodate the pivoting of the staple legs 60 from the vertical orientation (as shown in FIG. 21) to the horizontal orientation as the staple is advanced along the leg track 262.

As shown in FIG. 16, the staple array engaging member 68 projects upwardly from a feeder shoe or member 334, and the feeder shoe 334 is slidably disposed on the staple track member 274 as shown in FIG. 16B. The feeder shoe 334 is biased distally by the compression spring 66 acting between the engaging member 68 and the retainer washer 220.

The former plate 312 extends proximally out of the staple track member 274 as shown in FIGS. 17A and 18. As illustrated in FIG. 16, the former plate 312 has a notch 338 on one side. With reference to FIGS. 17 and 23, the notch 338 in the former plate 312 receives an inside edge of the retainer washer 220 as the cartridge is initially assembled by the cartridge supplier. However, after proper installation of the cartridge 80 on the stapler 50, which installation includes rotating the stapler cartridge housing 222 a predetermined amount as described hereinafter, the former plate notch 338 becomes disengaged from the retainer washer 320 and is oriented as shown in FIG. 40 so that the retainer washer 220 no longer prevents longitudinal movement, either distally or proximally, of the former plate.

As illustrated in FIG. 16, the proximal end of the former plate 312 has a reduced width neck 340 and a wider head 342 at the proximal end of the neck 340. As shown in FIGS. 17 and 17A, the former plate neck 340 and head 342 are inserted into the flexible cable connector 196. The connector 196 includes a distal end aperture 344 which communicates with a transverse aperture 346 on one side and a transverse aperture 348 (FIG. 17B) on the other side.

During installation of the cartridge 80 according to a novel method described in detail hereinafter, the proximal end of the former plate 312 is inserted into the connector aperture 344 and then rotated with the cartridge 80 relative to the connector 196 to re-orient the former head plate 342 in a generally transverse relationship relative to the aperture 344 as illustrated in FIG. 17B. In this orientation, the wider head 342 extends into the lateral apertures 346 and 348 as shown in FIG. 17B, and the former plate 312 and connector 196 are then engaged so that the former plate 312 can be moved distally or proximally with the connector 196 in response to the operation of the actuator mechanisms in the handle as described in detail hereinafter.

The distal end of the former plate 312 is adapted to engage and advance a staple 52 in cooperation with the staple track and other guide surfaces defined in the cartridge housing 222. As illustrated in FIGS. 16 and 26, the staple track member 274 defines a distal surface 360 inclined at an angle relative to the longitudinal axis of the staple track 262 in the cartridge nose 260. The inside of the cartridge housing 222 defines a similarly inclined surface 362 which is spaced from, and parallel to, the surface 360. The staples 52 are urged down the path defined between the inclined surfaces 360 and 362 by the feeder shoe 334 under the influence of the compression spring 66 (FIG. 18).

The most distal staple 52 is designated 52A in FIG. 26 and is shown received in the cradles 326 of the pickup spring 314. It will be recalled that, with reference to FIG. 2, each staple 52 has an upwardly arcuate hump 58, and this is shown in cross section in FIG. 26. FIG. 2 also illustrates each staple 52 as having lower crown end portions 56 extending laterally from the hump 58. The lower crown end portions 56 are received in the pickup spring cradles 326 in FIG. 26.

With reference to FIG. 26, it will be noted that the distal engaging ends 70 of the former plate 312 are retracted slightly from the distal end of the receiving slot 310 defined in the staple track member 274. In the orientation illustrated in FIG. 26, the former plate 312 is fully retracted, the trigger lever 104 (FIG. 1) is in the fully released, unactuated position, and the stapler is ready to advance and apply the lead staple 52A.

FIGS. 27–30 illustrate advancement of the lead staple 52A as the former plate 312 is moved distally in response to squeezing the trigger lever 104 (which controls the motion of the former plate 312 through mechanisms in the handle which are described in detail hereinafter). As shown in FIG. 27, the former plate distal end engaging members 70 move forwardly next to the outside edges of the pickup spring 314 and engage the crown end portions 56. This causes the pickup spring 314 to deflect transversely (e.g., downwardly) somewhat. The staple 52 immediately behind the lead staple 52A is prevented from moving down the angled surface 360 by the top surface of the former plate 312 which slides beneath the second staple 52.

Because the lead staple crown end portions 56 are held in the pickup spring 314, the lead staple 52A moves at an angle with a distal component of motion (as well as with a downward component of motion) to the extent that the pickup spring 314 deflects distally and transversely (e.g., downwardly). The distal deflection of the spring vertical portion 320 (FIGS. 16 and 18) provides the required slight distal movement of the pickup spring cradles 326 carrying the staple. This accommodates travel of the lead staple 52A down the angled path between the two inclined surfaces 360 and 362. The staple 52A remains generally in the vertical orientation with its legs 60 pointing transversely (e.g., downwardly) in the position shown in FIG. 27. The staple could, however, have a slight forward angle.

The staple hump 58 is engaged with the inclined surface 362 as shown in FIG. 27. As the staple 52A moves further downwardly, the staple hump 58 slides along the angled surface 362 until it engages the angled surface 362 at the proximal end of the longitudinal rib 328. As the engaging ends 70 of the former plate 312 advance further distally as shown in FIG. 28, the staple crown end portions 56 enter the bottom of the staple track 262 and are supported on the upwardly facing, horizontal surfaces of the staple track 262 as well as on the coplanar top surface of the anvil plate portion 294. This terminates the transverse (e.g., downward) movement of the lead staple 52A.

As the former plate engaging ends 70 continue to advance, the staple crown end portions 56 begin to be pushed along the staple track 262. However, the hump 58 is still engaged with the angled surface 362 at the proximal end of the rib 328. The staple 52A thus begins to rotate with the crown end portions 56 serving as a pivot. The hump 58, as it tips to the horizontal position, is received in the recess between the engaging ends 70 of the former plate 312 (see the recess visible in FIG. 16).

FIG. 29 illustrates further distal movement of the former plate 312 which causes the staple hump 58 to be pivoted completely down to the staple track 262, and this causes the staple legs to be oriented horizontally and point in the distal direction along the staple track 262. The staple legs swing upwardly in the cartridge housing slots 332 (FIGS. 16B and 20). As noted previously, the former plate 312 has an upwardly open channel 230 (FIG. 16) to accommodate the downwardly depending rib 328 as the former plate 312 moves below the rib 328 in FIGS. 28–30.

As illustrated in FIG. 30, when the staple former plate 312 is advanced to the distal end of the stapler, the crown end portions 56 are bent against the projecting anvil arms 72 to close the staple (into the configuration described above with reference to FIG. 3).

As the staple is pushed against the anvil arms 72 and closed, the ejector spring arms 286 are depressed by the staple. When the trigger lever 104 is released, the staple former plate 312 is retracted by a spring in the handle 86 (as described in detail hereinafter). The ejector spring arms 286 are then free to spring upwardly to the unstressed position, and this assists in separating the closed staple from the nose of the stapler.

INSTALLATION OF THE STAPLE CARTRIDGE ON THE STAPLER WITH A DEDICATED LOADING TOOL

A stapler 50 may be initially provided to the user with a stapler cartridge 80 installed thereon. If desired, the empty stapler cartridge 80 may be removed and replaced with a new staple cartridge full of staples. The novel method for installing a new cartridge with a special tool may be employed as next described.

FIG. 31 illustrates a special tool or loading sleeve 370 which is adapted to receive a cartridge 80. The cartridge 80 is initially supplied with the internal components shown in FIG. 16 completely assembled within the cartridge. The proximal end head 242 of the staple former plate 312 projects beyond the proximal end of the cartridge 80 as illustrated in FIG. 6.

The staple former plate 312 and the other components within the cartridge housing 222 are initially oriented in a predetermined relationship relative to the rotational position of the surrounding cartridge housing 222. During the process of loading the cartridge 80 onto the end of the stapler, that initial orientation is changed as the cartridge is locked onto the stapler in a manner described in more detail hereinafter.

The loading sleeve 370 has a generally hollow configuration with a generally cylindrical distal end portion 372 and a proximal end portion 374. Although the exterior surface of the proximal end portion 374 of the loading sleeve 370 has a frustoconical configuration, the internal configuration of the proximal end portion 374, as well as the internal configuration of the distal end portion 376, is cylindrical. The loading sleeve 370 has a constant internal diameter along its length.

At the open end of the distal portion 372 there is an L-shaped engaging lug 377 on the inside surface. The lug 377 is adapted to engage the distal end of the cartridge housing 222.

The loading sleeve proximal portion 374 has a pair of opposed spring arms 376 and 378. Each spring arm 376 and 378 is defined by longitudinal slots on either side which separate the spring arms from the remaining wall. The distal end of the spring arm 376 has an engaging nose 380. Similarly, the distal end of the spring arm 378 has an engaging nose 382.

As presently contemplated, the preferred form of the loading sleeve 370 is a molded component which may be molded from a suitable material, such as a polycarbonate polymer.

FIGS. 31–36 and 41–47 show the loading sleeve 370 in conjunction with the cartridge 80 wherein the internal components of the cartridge 80 have been omitted for ease of illustration. As illustrated in FIG. 33, the loading sleeve 370 is installed on the distal end of the cartridge 80 so that the L-shaped lug 377 engages the left-hand, upper, distal corner of the cartridge housing 222 (as viewed in FIG. 33). It is contemplated that the loading sleeve 370 may be installed by the manufacturer on the cartridge 80 and packaged in that manner for distribution to users. In any event, when properly installed on the cartridge 80, the loading sleeve spring arms 376 and 374 extend along the outer surface of the cartridge 80. The spring arm nose 380 is received in the cartridge window 232 while the spring arm nose 382 is received in the cartridge window 234. This effectively latches the loading sleeve to the cartridge 80, and it would be extremely difficult to disengage the two components merely by attempting to pull them apart by hand.

With the loading sleeve 370 and cartridge 80 engaged as described above, the two components are moved together axially onto the projecting distal portion of the swivel idler 180 (which is mounted at the end of the stapler in the shells 156 and 158 (FIG. 6) as described above in detail).

As the user pushes the cartridge 80 axially onto the swivel idler 180 by holding and pushing on the loading sleeve 370, the user also turns the loading sleeve 370 in the direction required to engage a conventional right-hand thread. The rotation of the cartridge 80 relative to the swivel idler 180 permits the cartridge housing ribs 241, 242, 243, and 244 (FIGS. 31, 32, and 47) to rotate to the orientation wherein they will pass axially alongside and between the swivel idler lugs 211, 212, 213, and 214 (FIG. 31).

As the loading sleeve 370 and engaged cartridge 80 are rotated against the swivel idler 180, the swivel idler 180 does not rotate because the axial force exerted during the cartridge loading process causes engagement of the idler notches 188 (FIGS. 33, 41, 44, and 45) with the shell teeth 186 (FIGS. 41–45) as previously described. Thus, the cartridge 80 can rotate as necessary against, and relative to, the stationary idler 180 as the cartridge ribs line up with the spaces between the idler lugs to permit complete axial insertion of the cartridge 80 onto the idler 180.

It will be appreciated that during the installation process so far described, it is not possible to remove the loading sleeve 370 from the cartridge 80 by merely manually pulling on the components. Thus, until the cartridge 80 is locked onto the idler 180, any attempt to pull the loading sleeve 370 distally will necessarily carry with it the engaged cartridge 80. This is a safety feature that prevents the cartridge 80 from being released and exposed for use unless and until it is properly locked on the idler 180 as described in detail hereinafter. If the loading sleeve is not removed, the instrument would have too large a diameter at the distal end to be inserted into a standard trocar for which the instrument is designed.

When the cartridge 80 has been aligned as necessary so that the cartridge ribs 241, 242, 243, and 244 can pass between the idler lugs 211, 212, 213, and 214, and when the aligned cartridge 80 has been advanced axially completely onto the idler 180, the components have the orientation as illustrated in FIG. 35. FIG. 35 shows that the deflectable portion 202 of the swivel idler 180 has been deflected inwardly by an overlapping portion of the proximal end of the cartridge housing 222. This occurs because the proximal, open end of the cartridge housing 222 is sufficiently resilient to be deflected outwardly slightly over the thicker flange 202. When the loading sleeve 370 is in the most proximal position, the loading sleeve engaging noses 380 and 382 are still engaged within the cartridge windows 232 and 234 as illustrated in FIG. 36.

In order to lock the cartridge 80 onto the idler 180, the loading sleeve 370 is rotated, along with the cartridge 80, counterclockwise as viewed in FIGS. 35, 36, and 42. This positions the cartridge housing proximal notch 250 (FIG. 35) into precise alignment with the idler deflectable portion 202 so that the deflectable portion 202 springs outwardly as viewed in FIG. 41 and is received in the notch 250. This prevents the cartridge housing 222 from being rotated in either direction unless the deflectable portion 202 is subsequently pushed radially inwardly by the user's finger as the cartridge housing 222 is rotated.

In the rotated position of the cartridge 80 illustrated in FIGS. 41, 46, and 48, the cartridge ribs 241, 242, 243, and 244 are axially aligned behind the swivel idler lugs 211, 212, 213, and 214, respectively. This prevents the cartridge from being pulled axially off of the idler 180.

When the cartridge housing 222 is rotated to the locked position as shown in FIG. 41, the loading sleeve spring arms 374 and 376 are cammed outwardly as shown in FIG. 42. In particular, the nose 382 on the spring arm 374 is cammed outwardly by the exterior surface of the idler lug 214. The nose 380 of the spring arm 376 is cammed outwardly by the idler lug 212. The amount of outward camming of the spring arms 374 and 376 is sufficient to permit the noses 380 and 382 to be withdrawn beyond the distal edges of the associated cartridge housing windows 232 and 234, respectively, when an axial retraction force is applied to the loading sleeve 370. The loading sleeve 370 can thus be pulled off of the installed cartridge 80 as illustrated in FIG. 43. As the loading sleeve 370 is pulled off, the cam arms 374 and 376 are deflected even further outwardly as the noses 380 and 382 ride up over the distal edges of the windows and onto the exterior cylindrical surface of the cartridge 80.

It will be appreciated that, during the process of rotating the cartridge 80 to properly align it on the swivel idler 180 and pushing the cartridge on, the internal components must be maintained in an orientation that will initially allow the projecting, proximal end head 342 of the staple former plate 312 to be longitudinally restrained and enter into the connector 196 inside the swivel idler 180. The cartridge ribs 241, 242, 243, and 244 and the cooperating idler lugs 211, 212, 213, and 214 are designed to axially slide past one another in the rotation orientation that necessarily results in the former plate head 242 entering the distal end aperture 344 in the connector 196.

The installation process must also subsequently accommodate the rotation of the former 10 plate 312 relative to the connector 196 to effect an engagement between the two parts so that the staple former plate 312 can be reciprocated within the stapler cartridge 80 in response to movement of the connector 196 as controlled from the stapler handle 86. To this end, the novel retainer washer 220 (FIG. 16) is employed to cooperate with the cartridge housing 222 and the notch 338 in the staple former plate 312.

In particular, when the cartridge 80 is assembled prior to installation on the stapler, the staple former plate 312 and other components within the cartridge 80 are provided in a predetermined orientation relative to the cartridge housing 222. This initial orientation is illustrated in FIGS. 37–39. In this orientation, the staple former plate notch 338 engages a radially inwardly extending flange segment 383 on the inside peripheral portion of the retainer washer 220 (FIGS. 38 and 39). The circumferential periphery of the retainer washer 220 is frictionally engaged with the inside cylindrical surface of the cartridge housing 222. The washer 220 is also retained on its proximal side by distal ends of the cartridge ribs 241 and 243 (FIG. 37). The washer 220 is also retained on its distal side by engagement with the proximal ends of the cartridge housing internal guide surfaces and walls, such as the ends of the shoulder 268 and tracks 264 shown in FIG. 16A (from which figure the washer 220 has been omitted for ease of illustration). Because the notch 338 of the staple former plate 312 receives the inside edge of the flange segment 383 of the retainer washer 220 which is frictionally restrained against rotational movement within the cartridge, the staple former plate 312 is locked against longitudinal movement.

The staple former plate 312 is disposed, as previously described, within the slot 310 in the staple guide track 274 (FIGS. 16, 18, and 21). The staple track member 274 is mounted in the interior of the cartridge housing 222 and cannot rotate relative to the cartridge housing 222 owing to the engagement of the various mating surfaces (see FIG. 21, for example). Thus, the staple former plate 312, along with the other components within the staple track member 274, cannot rotate relative to the cartridge housing 222.

The retainer washer 220, although frictionally engaged with the inside of the cartridge housing 222, can rotate relative to the cartridge housing 222 if a sufficiently high torque is applied to the washer 220. Such torque can be applied by engaging the recessed retainer washer 220 and holding it fixed while the cartridge housing 222 is rotated. Such an engagement of the recessed washer 220 can be effected with the lugs 216 and 218 (FIG. 31) which project distally from the distal face of the swivel idler 180. In particular, when the cartridge is initially pushed completely onto the swivel idler as explained above with reference to FIGS. 31–36, 41, 42, and 43, the swivel idler distal face lugs 216 and 218 enter recesses 386 and 388, respectively, defined in the retainer washer 220 (as shown in FIG. 39).

Next, when the cartridge housing 222 is rotated with the loading sleeve 370 to lock the cartridge 80 onto the idler 180, the idler distal face lugs 216 and 218 prevent the retainer washer 220 from rotating with the cartridge housing 222. It will be recalled that when axial force is applied to push the cartridge housing 222 onto the idler 180, the idler 180 is prevented from rotating by engagement between the idler flange notches 188 (FIG. 41) and the shell teeth 186 (FIGS. 44 and 45). Thus, the idler face lugs 216 and 218 and washer 220 cannot rotate as the cartridge housing 222 rotates to the locked position. Thus, as shown in FIG. 40, when the cartridge housing 222 is rotated (in the direction of the arrows shown in FIG. 40), the cartridge housing 222 and internal components (including the staple former plate 310) also rotate, but the retainer washer 220 is prevented from rotating by the lugs 216 and 218. As a result, the staple former plate 312 rotates out of engagement with the flange segment 383 of the retainer washer 220 (i.e., the staple former plate notch 338 is moved clear of the retainer washer 220 as shown in FIG. 40).

As the staple former plate 312 rotates to the position illustrated in FIG. 40, the former plate proximal end head 342 (FIGS. 17A and 17B) rotates sufficiently behind the slot 344 into the apertures 346 and 348 in the connector 196 so as to establish an engagement between the staple former plate 312 and the connector 316 that permits the staple former plate 312 to be moved distally and proximally by the connector 196.

When it is desired to remove an empty cartridge 80, the deflectable portion 202 (FIG. 43) of the idler 180 can be pushed inwardly (by one's finger) as the cartridge is rotated part way over the portion 202 and then pulled off.

THE SHAFT ROTATION MECHANISM

The shaft portion 84, which includes the cartridge 80 at the distal end, is rotatable relative to the handle 86 by rotation of the hollow knob 100 (FIG. 1). As illustrated in FIGS. 1, 5, and 11, the knob 100 includes an enlarged, frustoconical proximal end 602 disposed on the necks 128 and 126 of the handle sections 87 and 89, respectively. The knob 100 has a reduced diameter distal end section 604 which is disposed on the tube 120.

The knob 100 is retained on the tube 120 against the handle 86 by engagement with the driver 133 (FIGS. 5, 11, 12, 13, 14, and 15). It will be appreciated that the driver 133 as illustrated in FIG. 5 has been rotated 180° around its longitudinal axis compared to the orientation of the driver 133 shown in FIGS. 12–15.

The driver 133 includes two outwardly projecting pins which are adapted to be received in the apertures 132 in the tube 120 (FIG. 5). When properly installed, the driver pins 606 project through the apertures 132 beyond the exterior circumference of the tube 120 as shown in FIGS. 7, 12, and 14. The driver 133 is preferably fabricated from a thermoplastic material and is sufficiently flexible and resilient to accommodate its insertion into the tube 120 with the pins 606 projecting through the tube apertures 132.

As illustrated in FIGS. 7 and 14, the distal end of the knob 100 defines a pair of recesses 608 for each receiving one of the pins 606. Each recess 608 is open distally but has a proximal wall 610 for engaging the proximal side of the pin 606 received therein. This holds the knob 100 on the handle neck sections 126 and 128, and this prevents the knob 100 from moving distally along the tube 120.

As illustrated in FIG. 14, each recess 608 has a circumferential arc width which is greater than the circumferential arc width of the pin or lug 606. This establishes a predetermined amount of lost motion angular displacement between the pins or lugs 606 and the knob recesses 608. This lost motion capability is employed when the knob 100 is rotated in one direction or another about the longitudinal axis to effect rotation of the tube 120 as described in more detail hereinafter.

As illustrated in FIGS. 5 and 12, the driver has first and second arms 611 and 612, respectively, which are separated by a notch 614. This allows the arms 611 and 612 to be deflected inwardly somewhat when the driver 133 is initially installed in the tube so that the arms can slide along the inside of the tube until they are aligned with the tube slots 130. The arms 611 and 612 then spring outwardly through the slots 130 as illustrated in FIGS. 12 and 13 to engage teeth 624 in the handle sections 126 and 128. The arms 611 612 also deflect inwardly as required to be disengaged from the teeth 624 during certain modes of operation as described in detail hereinafter.

The first arm 611 includes a distal engaging surface 616 as shown in FIG. 15 and has a distal deflection surface 618 (FIG. 15). Similarly, the second arm 612 has an engaging surface 620 and a deflection surface 622 (FIG. 15). The deflection surface and engaging surface of each arm converge to define a distal end, and the distal end of each arm is adapted to be received between adjacent pairs of the teeth 624 defined on the inside of the handle neck sections 126 and 128 as illustrated in FIGS. 13 and 15.

When the arms 611 and 612 are in their normal, unstressed condition, the distal ends of the arms extend outwardly and are received between a pair of adjacent teeth 624. The engaging surface 616 of the first arm 611 is adapted to engage the side of one of the teeth 624. Similarly, the engaging surface 620 of the second arm 612 is adapted to engage the side of one of the teeth 624.

Owing to the configuration of the engaging surface 616 at the end of the first arm 611, the driver 133 from which the arm projects cannot rotate in the clockwise direction as viewed in FIGS. 13 or 15. Similarly, owing to the orientation of the engaging surface 620 of the second arm 612, the driver 133 from which the second arm projects cannot normally be rotated in the counterclockwise direction as viewed in FIGS. 13 and 15. Thus, because the elongate tube 120 is connected in a fixed rotational configuration with the driver 133 via the driver pins 606, it is not possible to rotate the tube 120 relative to the handle 86 by merely applying torque to the tube 120 (as by attempting to grasp the distal end of the tube 120 and rotate the distal end of the tube 120). Rather, rotation of the tube 120 about its longitudinal axis can only be effected if an appropriate one of the arms 611 and 612 is first deflected inwardly out of engagement with the teeth 624.

Owing to a unique feature in the knob 100, the knob 100 can be rotated in the clockwise direction as viewed in FIGS.

13 and 15 to deflect the first arm 611 out of engagement with the teeth 624 and to subsequently effect rotation of the tube 120. In particular, the knob 100 includes an inwardly extending cam surface 626 for engaging the deflecting surface 618 of the first arm 611. The cam surface 626 extends from the distal end of the deflection surface 618 part way along the longitudinal length of the deflection surface 618 as shown in FIG. 12A. The proximal portions of the first arm deflection surface 618 and engaging surface 616 extend proximally beyond the knob cam surface 626 into the teeth 624 in the handle sections 126 and 128.

The knob 100 also defines a second cam surface 628 circumferentially spaced from the first cam surface 626 (FIGS. 12, 13, and 15). The second cam surface 628 is adapted to engage the deflection surface 622 of the second arm 612. The cam surface 628 extends from the distal end of the deflection surface 622 part way along the longitudinal length of the deflection surface 622. The proximal portions of the second arm deflection surface 622 and engaging surface 620 extend proximally beyond the end of the cam surface 628 and into the teeth 624 defined in the handle sections 126 and 128.

The knob 100 can be rotated clockwise as illustrated in FIG. 15 and indicated by the arrow 630. Initially, the knob 100 rotates slightly relative to the driver 133 (and relative to the arms 611 and 612 projecting therefrom) so as to bring the first cam surface 626 of the knob into the engagement with the deflection surface 618 of the first arm 611. The initial relative rotation between the knob 100 and the driver 133 occurs because the knob recesses 608 (FIG. 14) are wider than the pins 606 which project from the driver 133 into the engaging holes 132 in the tube 120. This provides a range of lost motion on either side of the pins 606. This lost motion permits an initial incremental rotation of the knob 100 to bring the knob camming surface 626 into engagement with the first arm deflection surface 618 for deflecting the first arm 611 inwardly out of engagement with the teeth 624.

During this initial movement, the driver 133, from which the first arm 611 extends, does not rotate because of the engagement between the first arm engaging surface 616 and a side of an adjacent tooth 624 which prevents rotation of the driver 133 until the engagement surface 616 has been deflected inwardly and has completely cleared the adjacent tooth 624. The width of the recess 608 (FIG. 14) is great enough to permit sufficient rotational movement of the knob 100 to deflect the arm 611 out of engagement with the teeth before the end of each recess 608 contacts the associated pin 606 of the driver 133.

When the first arm 611 is deflected inwardly to clear the teeth 624, the ends of the recesses 608 contact the pins 606 (FIG. 14), and the continued rotation of the knob 100 thus urges the pins 606, and the tube 120 engaged therewith, to rotate with the knob 100. As the tube 120 rotates, the driver 133 rotates with the tube 120, and the first arm 611 remains deflected inwardly as illustrated in FIG. 15 by the camming surface 626 of the knob 100.

While the tube and driver rotate, the deflection surface 62 of the second arm 612 is deflected inwardly by the teeth 624. In particular, with reference to FIG. 15, as the driver 133 and its second arm 612 rotate clockwise in the direction of the arrow 630, the second arm deflection surface 622 is carried past each tooth 624 seriatim. As the arm 612 rotates past a tooth 624, the arm 612 momentarily deflects inwardly and then springs back outwardly into the space between the tooth from which it became disengaged and the next tooth. The deflection and springing action is indicated by the double-headed arrow 632 in FIG. 15. The sequential inward deflection and outward springing of the arm 612 generates an audible click sound.

When the desired rotational orientation of the tube 120 has been achieved, the torque on the knob 100 is released. The first arm 611, owing to its inherent resiliency, springs outwardly against the cam surface 626 of the knob 100 and rotates the knob 100 in the reverse direction a very slight amount as may be necessary for the distal end of the first arm 611 to slide between a pair of adjacent teeth 624. In this position, the first arm engaging surface 616 can again engage an adjacent tooth 624 to prevent clockwise rotation of the tube 120 unless a clockwise torque is subsequently applied to the knob 100.

The second arm 612 also springs outwardly so that the engaging surface 620 of the second arm 612 can engage an adjacent tooth 624 and prevent rotation of the tube 120 in the counterclockwise direction unless a suitable counterclockwise torque is subsequently applied to the knob 100.

It will be appreciated that the knob 100 can be rotated in the counterclockwise direction (in the direction opposite to that indicated by the arrow 630 in FIG. 15) to effect rotation of the tube 120 in the counterclockwise direction. When the knob 100 is rotated in the counterclockwise direction, the knob second camming surface 628 cams the second arm 612 inwardly to disengage the second arm 612 from the teeth 624. At that point the lost motion between the knob slots 608 (FIG. 14) and the pins 606 has been taken up. Thus, continued rotation of the knob 100 in the counterclockwise direction (as viewed in FIG. 15) causes the driver 133 and connected tube 120 to rotated in the counterclockwise direction. As this occurs, the first arm 611 is deflected inwardly as its deflection surface 618 passes over each tooth 624, and this creates an audible click.

When the counterclockwise torque on the knob 100 is released, the second arm 612 springs outwardly, and the second arm deflecting surface 622 acts against the knob second cam surface 628 to rotate the knob 100 in the clockwise direction a small amount as may be necessary until the second arm distal end surfaces 620 and 622 again project between two adjacent teeth 624. The second arm engaging surface 620 can then engage the adjacent tooth to prevent counterclockwise rotation of the tube 120 while the first arm engaging surface 616 can engage an adjacent tooth 624 to prevent clockwise rotation of the tube 120.

The rotation of the tube 120 by the knob 100 effects rotation of the entire shaft portion 84 of the stapler 50, including the cartridge 80 at the distal end. There is sufficient friction between the internal components within the tube 120 that the cartridge 80 rotates with the shaft even though the cartridge 80 is independently rotatable relative to the tube 120. In particular, it will be appreciated that there is some degree of frictional engagement between the flexible cable 144 (FIG. 6) and the arcuate, receiving channel 174 in the pivotal shell 156 and in the arcuate receiving channel 142 of the pivot housing 134. Thus, when the tube 120 rotates and effects rotation of the pivot housings and shells mounted at the end of the tube 120, the flexible cable 144 rotates along with the tube, pivot housings, and shells.

The D-shaped connector 196 at the distal end of the flexible cable 144 necessarily also rotates and effects rotation of the swivel idler 180 to which the cartridge 80 is mounted. Similarly, the rigid rod 146 connected to, and extending proximally from, the flexible cable 144 also rotates with the flexible cable 144 along with the shells, pivot housings, and tube 120.

The articulation driver plate 167 which has a flat or substantially planar configuration, and which is slidably guided at its distal end between the pivot housing 134 and 136 and between the shells 156 and 158, necessarily rotates with those components as the tube 120 rotates.

CARTRIDGE ROTATION CONTROL

The staple cartridge 50 can rotate about its longitudinal axis at the distal end of the stapler to facilitate placement of a staple and tissue at a desired orientation. This is most useful when the stapler 50 has been articulated so that the staple cartridge 80 is at an angle relative to the longitudinal axis of the remaining length of the shaft portion 84 extending proximally from the cartridge to the handle 86. The distal end of the angled cartridge 80 can be moved to a desired location by rotating the tube 120 with the knob 100 as described above. However, rotation of the tube 120 necessarily changes the orientation of the cartridge 80, and independent rotation of the cartridge 80 relative to the tube 120 can position the staple discharge path in a desired orientation to facilitate application of the staples at a selected location.

As described above, the staple cartridge 80 is carried on the swivel idler 180, and the cartridge and idler rotate together about the axis of the idler within the shells 156 and 158. The swivel idler 180 can be rotated from the proximal end of the stapler handle 86 by the knob 96.

As previously explained with reference to FIGS. 6, 17, 17A, and 18, the operating rod distal end connector 196 has a generally D-shaped external configuration for being received in a mating D-shaped cavity in the rotatable idler 180 so as to establish an engagement between the two components which does not permit relative rotation between them. As illustrated in FIG. 10, the flexible cable 144 extends from the connector 16 to a generally rigid member or rod 636 which extends proximally to the knob 96. The connector 196, flexible cable 144, and rod 636 are preferably fabricated from stainless steel.

The rod 636 includes a proximal end portion having two flat sides 638 and 640 as shown in FIG. 5. As illustrated in FIG. 5, the knob 96 has an aperture with two, opposed, internal, flat walls 642 and 644 for engaging the rod sides 638 and 640, respectively. Thus, the rod 636 can be rotated by rotation of the knob 96. Access to the knob is provided on each side by an aperture in the handle sections, such as the aperture 646 illustrated in the handle section 89 in FIG. 5.

The cartridge rotation knob 96 has unitary stub shafts 637 (FIGS. 5 and 10) molded therein, and the shafts extend proximally and distally. The proximally extending portion of the shaft 637 is received at the proximal side of the knob 96 in a pair of cradle arms 639 (FIG. 10) extending from the handle section 89. The distally extending portion of the shaft 637 is received in a pair of cradle arms 641 extending from the handle section 89 on the distal side of the knob 96. The distal end of the knob shaft 637 is retained between the cradle arms 641 by a flange 643 (FIG. 5) projecting inwardly from the handle section 87. The proximal end of the knob shaft 637 is retained within the cradle arms 639 of the handle section 89 by an adjacent flange 645 (FIG. 5) projecting inwardly from the handle section 87.

Rotation of the rod 636 by the knob 96 necessarily effects rotation of the attached flexible cable 146 and connector 196 so as to rotate the idler 180 and cartridge 80 to the desired orientation. Owing to the employment of the flexible cable 144 through the pivot joint area of the pivot housings 134, 136 and shells 156, 158, the flexible cable 144 accommodates any articulated position and can be rotated by the knob 96 at any articulated position.

Although there is some amount of friction on the operating rod 146, especially as imposed on the flexible cable 144 by the pivot housing 134 and shell 156, the frictional resistance to rotation is easily overcome by the application of sufficient torque to the knob 96. The frictional resistance in the system does not cause the pivot housings 134, 136, shells 156, 158, and attached tube 120 to rotate with the cartridge 80 because the tube 120 is in effect locked against rotation by the previously described engagement of the tube driver arms 611 and 612 with the handle teeth 624 as shown in FIGS. 13 and 15. Thus, external rotational forces applied to the distal end of the tube 120, as by the rotation of the swivel idler 180 and cartridge 80 (or by any other torque applied to the exterior distal end of the tube 120) cannot cause a rotation of the tube 120. The tube 120 can only be rotated by rotation of the knob 100, as explained in detail above, so as to disengage the arm 611 or 612 from the teeth 624.

THE ARTICULATION CONTROL

As illustrated in FIG. 6, the articulation driver plate 167 extends from the pivotable shells 156 and 158 adjacent the distal end of the stapler toward the proximal end of the stapler. At the distal end, the articulation driver cam channel 165 receives the pin 164 of the pivotable shell 158. Retraction of the articulation driver plate 167 (from the position illustrated in phantom by dashed lines in FIG. 9 to the retracted position illustrated by solid lines in FIG. 9) drives the pin 164 in an arc to pivot the distal end of the stapler.

As shown in FIG. 6, the articulation driver plate 167 has a distal end portion 648 which is laterally offset from the flexible cable 144. The articulation driver plate 167 has a proximal portion 650, as illustrated in FIG. 6, which is formed with a semi-cylindrical channel 652 for accommodating the adjacent rigid member 636 of the operating rod 146 extending from the flexible cable 144.

As illustrated in FIG. 6, the articulation driver plate proximal portion 650 and the operating rod rigid member 636 are supported within the tube 120 by a support member 654. The support member 654 is preferably fabricated from a polymeric material, such as polycarbonate. The member 654 has a central cavity defined by arcuate surfaces 656 for receiving the cylindrical shape of the rigid member 636. On each side of the longitudinal cavity there is a shoulder 658 extending laterally from one of the arcuate surfaces 656. Each shoulder 658 supports a lateral margin of the articulation driver plate 167.

As shown in FIGS. 9 and 10, the proximal end of the driver plate 167 defines a vertical slot 660. As illustrated in FIGS. 5 and 9A, the articulation driver plate 167 has an outwardly bowed flange 662 which curves outwardly in a direction opposite from the semicylindrical channel 652 (FIG. 5). The flange 662 defines the distal end of the vertical slot 660 as shown in FIGS. 9 and 10.

An articulation slide 664 is slidably engaged with the handle sections 86 and 87, and the slide 664 is engaged with the proximal end of the articulation driver 167 at the slot 660 and flange 662 as illustrated in FIGS. 9 and 9A. FIG. 5 shows that the articulation slide 664 includes a generally flat plate 666 having a longitudinal rib 668 projecting downwardly from the underside of the plate 666. Projecting upwardly from the distal end of the plate 666 is a tooth 670 which has a thin, arcuate engaging edge 672. The distal end of the articulation slide plate 666 has a downwardly depending flange 674.

As illustrated in FIG. 9A, the front of the flange 674 defines a vertical slot 676 for receiving the rigid member portion 636 of the operating rod 146 and for accommodating passage of the rigid member 636 below the articulation slide rib 668. As shown in FIG. 9, a post 676 projects distally from the front face of the flange 674 and has an enlarged, distal head 678 which is cylindrical in shape. The head 678 is received in the slot 660 at the proximal end of the articulation driver plate 167. The post 676 is accommodated on one side by the outwardly bowed flange 662 at the proximal end of the vertical slot 660. The outwardly bowed flange 662 is thus trapped between the front face of the articulation slide flange 674 and the proximal side of the cylindrical head 678 of the articulation slide 664. This arrangement couples the articulation slide 664 to the articulation driver plate 167 to prevent relative longitudinal movement between the two components but to permit relative rotational movement between the two components.

The rib 668 is received in a drive link 661 (FIGS. 5 and 9) below the plate 666. As illustrated in FIGS. 5 and 10, the link 661 has a longitudinal slot 663 for receiving the rib 668. The slot 663 has a wider central portion 659 (FIG. 5).

The bottom surface of the articulation slide plate 666 is disposed above, and can slide relative to, the top of the link 661 on either side of the slot 663.

The link 661 has a pair of laterally projecting flanges 665 (FIG. 5) which support the link 661 in the handle 86. To this end, the handle section 87 defines a pair of longitudinally extending flanges 680 and 682 defining a guide track for receiving one of the link flanges 665. The other handle section 89 defines a similar pair of flanges (not visible in FIG. 5) for receiving the other flange 665 of the link 661.

The articulation driver plate 167 rotates about its longitudinal axis with the stapler tube 120, but the rotatably connected articulation slide 664 is restrained against rotation within the handle 86 by its sliding engagement with the handle sections 86 and 87.

Through a novel mechanism that is next described in detail, the articulation slide 664 can be reciprocated in the directions indicated by the double-headed arrow 684 in FIG. 9 from a retracted position shown in solid lines in FIG. 9 to an extended position shown in phantom by dashed lines in FIG. 9. This effects reciprocation of the articulation driver plate 167.

The articulation slide 664 is moved between its most proximal position and its most distal position in the handle 86 by control mechanism components illustrated in FIG. 5. These include a helical gear 686, a first bevel gear 688 integral with, and projecting from, the distal end of the helical gear 686, a second bevel gear 690 engaged with the first bevel gear 688, a knob 92 integral with, and extending laterally from, the second bevel gear 690, and a second knob 94.

The helical gear 686 defines a helical groove 696 which receives the thin, arcuate edge 672 of the tooth 670 projecting upwardly from the articulation slide 664. The tooth edge 672 engages the helical gear 686 within the stapler and accommodates rotation of the helical gear 686 as the tooth 670 is driven distally or proximally by the rotating helical gear 686.

In the preferred embodiment illustrated in FIG. 9, the pitch of the helical gear groove 696 is not constant over the length of the gear. Rather, the pitch decreases toward the distal end of the helical gear 686. That is, the helical gear pitch decreases in the direction of retraction of the articulation slide 664, and hence, in the direction of retraction of the articulation member or plate 167. This provides a greater mechanical advantage as the articulation driver plate 167 is pulled in the proximal direction.

With reference to FIG. 9, the retracted, most proximal position of the articulation driver plate 167 corresponds to the fully articulated position of the cartridge 80. At and near the fully retracted position of the articulation driver plate 167, the increased pitch of the helical gear groove 696 accommodates the increased force that is required as retraction of the driver plate 167 increases the articulation angle ø (FIGS. 1 and 9). Further, this serves to hold the articulated distal end of the stapler at the selected angular position ø. That is, owing to the greatly increased pitch of the helical gear portion corresponding to the increased articulation angle ø, it is not possible for an external force acting on the articulated distal end of the stapler to overcome the engagement between the helical gear 686 and articulation slide 670 so as to move the cartridge 80 away from the selected angular orientation.

The helical gear 686 can be rotated by turning either of the knobs 92 or 94. The knob 94 is mounted for rotation in a bore 699 (FIG. 5) defined in the sidewall of the handle section 89. The knob 92 is mounted in a similar bore (not visible in FIG. 9) in the handle section 87. The knob 92 includes a shaft 698 projecting from the center of the second bevel gear 690, and the knob 94 is mounted to the shaft 698. The shaft 698 has a projecting rib 702, and the knob 94 has a mating internal aperture for being keyed on the shaft 698 with the rib 702. Thus, rotation of either knob 92 or 94 will cause the other knob and second bevel gear 690 to rotate while the gear 690 is engaged with the first bevel gear 688, and this will rotate the helical gear 686 to drive the articulation slide 664 proximally or distally depending upon the direction of knob rotation.

STAPLE ACTUATION CONTROL MECHANISM

The dual function operating rod 146 (FIGS. 1, 5, 10, and 11) is moved between a most proximal position and a most distal position to advance and form the staples 52 (FIG. 16), and that longitudinal movement of the operating rod 146 occurs in response to the squeezing of the trigger lever 104 from the unactuated position shown in phantom in dashed line in FIG. 7 to the actuated position shown in solid lines in FIG. 8.

As shown in FIGS. 5 and 10, the dual function operating rod 146 has an enlarged diameter section 636C between two reduced diameter sections 636A and 636B. The enlarged diameter section 636C is received in the enlarged groove 659 of the driver 661 as illustrated in FIG. 10. The driver 661 and operating rod 146 are thus movable together proximally and distally along the longitudinal axis of the stapler. However, while the operating rod 146 can rotate about the longitudinal axis relative to the driver 661, the driver 661 cannot rotate owing to the mounting of the driver lugs 665 in the handle section guide tracks (e.g., as shown in FIGS. 5 and 7 for the handle section 87 wherein one guide track is defined between the ribs 680 and 682).

The driver 661 is connected on each side to a pair of links 704 (FIGS. 5, 7, and 8). Each link 704 has a proximal end defining an aperture 706. The driver 661 has a pair of laterally projecting stub shafts 708 which are each received in one of the link apertures 706.

As shown in FIG. 5, the proximal end of each link 704 defines an aperture 710. As shown in FIG. 5, each link aperture 710 receives an end of a pin 714, and the central portion of the pin 714 is received in a cam channel 718 defined in the upper, proximal portion of the trigger lever 104. The pin 714 extends toward the handle section 87 beyond the adjacent link 704, and the extending end of the pin 714 is received in a guide channel 720 defined on the inside of the handle section 87 (FIG. 5).

The trigger lever cam channel 718, in a preferred embodiment, includes a generally straight portion 722 and a shorter, arcuate portion 724 (FIG. 7). Similarly, as shown in FIG. 5, the handle section guide channel 720 includes a generally straight portion 726 and a shorter, arcuate portion 728. The guide channel 720 in the handle section 87 and the cam channel 718 in the trigger lever 104 lie generally in parallel planes, and a portion of the cam channel 718 overlaps a portion of the guide channel 720 at any pivoted position of the trigger lever 104.

The trigger lever 104 is pivotally mounted to the frame with a pair of stub shafts 730 (FIG. 5) which are each received in a hollow, tubular socket in the adjacent handle section. Such a mounting socket 732 is shown in FIG. 5 for the handle section 87.

As shown in FIGS. 5, 7, and 8, a torsion spring 734 is disposed within the handle sections 87 and 89. The upper end of the spring 734 is coiled around one of the stub shafts 730 at the top of the trigger lever 104. The spring 734 has a short, first end 736 as shown in FIG. 5, and the first end 736 extends downwardly out of an opening in the front of the handle section 89 to engage a rear surface 738 of the front wall of the trigger lever 104.

As illustrated in FIG. 7, the spring 734 has a second end 740 which extends downwardly in the handle sections and engages a tubular sleeve 742 (FIGS. 5 and 7). As illustrated in FIG. 7, the spring first end 736 tends to bias the handle lever 104 outwardly (to the left as viewed in FIG. 7) while the spring second end 740 tends to bias the handle sections in the opposite direction (to the right as viewed in FIG. 7).

In an initial, unactuated position illustrated in FIG. 7, the trigger lever cam channel 718 is offset from the trigger lever pivot shafts 730, the handle section guide channel 720 is offset from the handle lever pivot shafts 730, and the pivot connections at each end of the links 704 are offset from the trigger lever shafts 730. Further, the pin 714 is substantially at the proximal end of the straight section 722 of the trigger lever cam channel 718 and is substantially at the bottom end of the arcuate section 728 of the handle section guide channel 720.

When the trigger lever 104 is squeezed, the cam channel 718 of the lever 104 forces the pin 714 generally in the counterclockwise direction (as viewed in FIGS. 7 and 8). The pin 714 travels along the handle section guide channel 720 and approaches the end of the straight section 726 of the guide channel 720 (FIG. 8). At the same time, the trigger lever cam channel 718 moves relative to the pin 714 so that the pin 714 is received in the proximal, arcuate section 724 of the trigger lever cam channel 718 when the trigger lever 104 has been squeezed through its full stroke.

The movement of the pin 714, in response to the squeezing of the trigger lever 104, effects distal movement of the links 704 (along with the connected driver 661). This moves the dual function operating rod 146 distally to advance and form the staples with the staple former plate 312 as has been previously described.

When the squeezed trigger lever 104 is released, the torsion spring 734 returns the trigger lever 104 back to the unactuated position as illustrated in FIG. 7, and this causes the pin 714, link 704, driver 661, and operating rod 146 to be pulled proximally to the unactuated position.

The novel arrangement of the trigger lever cam channel 718, pin 714, handle section guide channel 720, and links 704 provides a highly efficient and desirable transmission of forces for effecting operation of the staple former. In particular, during the end of the actuation stroke, as the trigger lever 104 approaches the palm grip 112 as shown in FIG. 8, it is desirable to provide a higher force to the stapler former plate 312 owing to the greater energy required at that point to bend the staple into the closed position. During much of the prior part of the stroke, a significantly lower force is sufficient to move the staple along the cartridge track to the anvil prongs (FIG. 18) at the distal end of the cartridge.

Accordingly, it is desirable to provide a relatively low mechanical advantage system for applying force during a major portion of the first part of the stroke and, at the same time, accommodate a relatively long stroke length as the staple is advanced along the cartridge. When the staple has reached the anvil, the remaining stroke length is very short as the staple is bent around the anvil prongs 72 (FIG. 30), but the force requirement is much greater. The above-described component design and arrangement in the preferred embodiment of the stapler of the present invention efficiently accommodates these requirements.

Further, when the trigger lever is released, the torsion spring 734 must have sufficient torque to pull the operating rod 146 proximally. Near the end of the return stroke (as the trigger lever 104 returns to the unactuated position in FIG. 7), significant torque may be required to insure that the friction in the system is overcome and that the staple former plate 312 is completely retracted to its home position in the cartridge 80. While the use of a very strong torsion spring may provide the required torque, the use of such a higher torque spring would necessarily require a greater squeezing force on the trigger lever 104 during the initial actuation stroke. The higher squeezing force can be objectionable, and the use of a larger spring to provide the greater torque may require larger housing components.

According to one aspect of the present invention, the preferred embodiment of the stapler does not require a higher torque spring because the handle guide channel 720 includes the short arcuate section 728 which multiplies, or otherwise increases, the torsion spring force at the end of the return stroke (and, necessarily, at the very beginning of the actuation (squeezing) stroke). With this design, the friction in the system, especially the friction between the flexible cable 144 (FIG. 11) and the channel 142 in the pivot housing 134 and channel 174 in the shell 156, can be overcome at the end of the return stroke to insure that the staple former plate 312 is fully retracted. This permits the use of a smaller torsion spring.

An alternate, and presently preferred, trigger lever cam channel is illustrated in FIGS. 7D and 7E. The alternate cam channel is designated generally by reference number 718'. The channel 718' has a first straight portion 722' and a second straight portion 724' which is oriented at an oblique angle relative to the first straight portion 722'.

The trigger system also includes a mechanism to prevent return of the trigger lever 104 until the full actuation (squeezing) stroke has been completed. This insures that each staple must be completely advanced and formed before the next staple can be advanced. This mechanism includes a pre-cock spring 746 which is positioned at the back of the trigger lever 104 as illustrated in FIGS. 5 and 7.

The upper end of the pre-cock spring 746 has a tubular configuration 748 (FIGS. 7A and 7B). The tubular configuration 748 is disposed in the upper end of the trigger lever 104 in a bore 750 which is open to one side of the trigger lever 104 as illustrated in FIG. 7A. The pre-cock spring 746 extends downwardly inside the palm grip section 112 of the handle. The lower end of the spring 746 has a distally extending pawl or engaging blade 752. The pawl 752 is adapted to engage teeth 754 which face proximally and which are defined along members 756 extending inwardly from each side of the handle sections 87 and 89 as illustrated in FIGS. 7 and 7C.

In the unactuated position of the stapler as illustrated in FIG. 7, the pre-cock spring pawl 752 is disposed below the bottoms of the teeth 754, and the extending length of the spring 746 is disposed proximally of the teeth 754. When the trigger lever 104 is squeezed, the spring 746 is pulled upwardly, and the pawl 752 is cammed proximally by the bottom ends of the toothed members 756 until the edge of the pawl 752 engages, and is pulled upwardly along, the teeth 754.

If the trigger lever 104 is released before the end of the stroke (i.e., before the trigger lever 104 has been pulled all the way to the right as viewed in FIG. 8), then the pawl 752 engages the next adjacent lower tooth 754, and this prevents the spring 746 from moving downwardly. This in turn prevents the trigger lever 104 from returning outwardly to the unactuated position.

In a preferred embodiment, one or both of the apertures 706 and 710 in the trigger links 704 are oval or slotted so as to provide a small amount of lost motion at the trigger lever shafts 730 and/or pin 714. This allows engagement of the spring 746 with the teeth 754 as soon as the trigger is initially pulled proximally, but prior to the trigger lever links 704 pushing the operating rod 146 distally. This eliminates the risk of feeding more than one staple with the former plate 312.

The trigger lever 104 can be released only by first squeezing it substantially all the way against the palm grip 112 as shown in FIG. 8 so as to raise the pawl 752 beyond the top of the teeth 754. At this point, the spring 746 is out of engagement with the teeth 754 and deflects distally to the position shown in solid lines in FIG. 8. With the trigger lever 104 squeezed against the palm grip 112, the lower end of the elevated pre-cock spring 746 is disposed distally of the toothed members 756. Thus, if the trigger lever 104 is then released, the pawl 752 is guided down the distal side of the members 756. About halfway down the members 756, the members 756 have a distally projecting cam surface 758. The spring pawl 752 has a proximal edge 760 (FIGS. 8 and 7C) which engages the distally projecting cam surface 758. This forces the bottom of the pre-cock spring 746 even further distally as the pawl 752 approaches the bottom of the members 756. The spring 746 is forced against a pin 762 (FIG. 8) in the handle section 87 as this occurs. At the bottom of the members 756, the proximal edge 760 of the pawl 752 clears the bottom of the cam surfaces 758, and the spring 746 moves proximally, owing to the reaction force of the pin 762 and owing to the spring's inherent resiliency, back to the initial position illustrated in solid lines in FIG. 7.

It will be readily apparent from the foregoing detailed description of the invention and from the illustrations thereof that numerous other variations and modifications may be effected without departing from the true spirit and scope of the novel concepts or principles of this invention.

What is claimed is:

1. In a surgical instrument for applying a surgical fastener from a cartridge that can be releasably attached to a mounting portion of said instrument and that contains a reciprocatable fastener advancing member adapted to be driven from an actuator on said instrument, a system for preventing longitudinal movement of said advancing member unless and until said cartridge is properly attached, said system comprising:

a housing integral with said cartridge and defining a path for reciprocation of said advancing member while restraining said advancing member against rotation relative to said housing;

a longitudinal restraint member retained in said housing against longitudinal movement relative to said housing and frictionally engaged with said housing to permit a relative angular displacement between said housing and said restraint member from a first angular orientation to a second angular orientation when a sufficient relative torque is applied between said restraint member and said housing, said restraint member defining a first anti-rotation engaging structure;

said mounting portion defining a second anti-rotation engaging structure for engaging said restraint member first engaging structure to prevent rotation of said restraint member relative to said mounting portion; and said advancing member and said restraint member engaging each other to prevent relative longitudinal movement when said housing and restraint member are in said first angular orientation and being disengaged in said second angular orientation whereby said cartridge can be attached to said mounting portion by first moving said cartridge with said housing axially onto said mounting portion to effect engagement of said first and second anti-rotation engaging structures which restrain said restraint member against rotation and by secondly rotating said housing relative to said restraint member from said first angular orientation to said second angular orientation to disengage said advancing member from said restraint member and thereby accommodate subsequent reciprocation of said advancing member.

2. The system in accordance with claim 1 in which said instrument frame includes a distally extending endoscopic tube;

said advancing member defines a lateral slot open to an edge of said advancing member;

said restraint member has a central opening through which said advancing member extends, said restraint member defining a flange segment extending radially inwardly and received in said slot when said advancing member and restraint member are in said first angular orientation but not in said second angular orientation;

said restraint member has two spaced-apart recesses which are open axially and define said first anti-engaging structure; and said mounting portion includes (1) a support pivotally attached to said tube and (2) a carrier that is received on said support and that has two spaced-apart, axially projecting lugs defining said second anti-rotation structure for being received in said restraint member recess.

* * * * *